United States Patent
Walt et al.

(10) Patent No.: US 6,720,007 B2
(45) Date of Patent: Apr. 13, 2004

(54) POLYMERIC MICROSPHERES

(75) Inventors: David R. Walt, Lexington, MA (US);
Tarun K. Mandal, Kolkata (IN);
Michael S. Fleming, Londonderry, NH (US)

(73) Assignee: Tufts University, Medford, MA (US)

( * ) Notice: Subject to any disclaimer, the term of this patent is extended or adjusted under 35 U.S.C. 154(b) by 0 days.

(21) Appl. No.: 10/033,389

(22) Filed: Oct. 25, 2001

(65) Prior Publication Data

US 2002/0172716 A1 Nov. 21, 2002

Related U.S. Application Data

(60) Provisional application No. 60/243,104, filed on Oct. 25, 2000.

(51) Int. Cl.[7] .................................................. A61K 9/14
(52) U.S. Cl. ..................... 424/489; 424/490; 424/497; 424/484; 424/486; 424/487; 424/724
(58) Field of Search ................................. 424/489, 490, 424/497, 724, 484, 486, 487

(56) References Cited

U.S. PATENT DOCUMENTS

| | | | |
|---|---|---|---|
| 3,423,489 A | 1/1969 | Arens et al. .................... 264/4 |
| 4,303,603 A | 12/1981 | Torobin ........................ 264/69 |
| 4,427,836 A | 1/1984 | Kowalski et al. | |
| 4,468,498 A | 8/1984 | Kowalaski et al. | |
| 4,594,363 A | 6/1986 | Blankenship et al. | |
| 5,360,827 A | 11/1994 | Toda et al. | |
| 6,001,312 A | 12/1999 | Wang et al. ................. 422/131 |
| 6,284,365 B1 * | 9/2001 | Hirose et al. ................ 428/333 |

FOREIGN PATENT DOCUMENTS

| | | |
|---|---|---|
| DE | 198 12 983 | 9/1999 |
| EP | 0 595 263 | 5/1994 |
| EP | 0549163 | 7/1994 |
| WO | WO 99/47253 | 9/1999 |

OTHER PUBLICATIONS

Auroy et al. (1991). *Physica A* 172: 269–284.
Bain et al. (1989). *J. of the Am. Chem. Soc.* 111: 321–335.
Bamnolker et al. (1997). *J. of Mat. Sci. Letters* 16: 1412–1415.
Caruso (2001). *Adv. Mater.* 13: 11–22.
Caruso et al. (1999). *Chem. Mater.* 11: 3309–3314.
Caruso et al. (1998). *Science* 282: 1111–1114.
Caruso et al. (1998). *J. of the Am. Chem. Soc.* 120: 8523–8524.
Caruso et al. (2000). *Langmuir* 16: 1485–1488.
Chen and Jenekhe (1999). *Langmuir* 15: 8007–8017.
Davis et al. (1998). *Nucleic Acids Res.* 26: 3915–3924.
Ding and Liu (1998). *Macromolecules* 31: 6554–6558.
Dubrovsky et al. (1999). *Anal. Chem.* 71: 327–332.
Ejaz et al. (1998). *Macromolecules* 31: 5934–5936.
Elghanian et al. (1997). *Science* 277: 1078–1081.
Ellman, G. (1958). *Arch. Of Biochem. & Biophys.* 74: 443–450.
Feng et al. (1996). *Sensors and Actuators B, Chem.* 35: 431–434.
Frens, G. (1973). *Nature Phys. Sci.* 241: 20–22.
Frey and Corn (1996). *Anal. Chem.* 68: 3187–3193.
Furusawa et al. (1994). *Colloid. Polym. Sci.* 272: 1104–1110.

(List continued on next page.)

*Primary Examiner*—Thurman K. Page
*Assistant Examiner*—Liliana Di Nola-Baron
(74) *Attorney, Agent, or Firm*—Ingrid A. Beattie; Mintz, Levin, Cohn, Ferris, Glovsky and Popeo P.C.

(57) ABSTRACT

The invention features core-shell microsphere compositions, hollow polymeric microspheres, and methods for making the microspheres. The microspheres are characterized as having a polymeric shell with consistent shell thickness.

7 Claims, 19 Drawing Sheets

OTHER PUBLICATIONS

Gill and Ballesteros (1998). *J. Am. Chem. Soc. 120*: 8587–8598.
Green, M. In *Adv. in Protein Chemistry;* Academic Press: New York, 1975, vol. 29, 85–133.
Hahner et al. (1993). *Langmuir 9*: 1955–1958.
Hall et al. (2000). *Langmuir 16*: 1454–1456.
Harding, R. (1972). *J. Colloid. Interface Sci. 40*: 164–173.
Harris et al. (1987). *Chem. Phys. Letters 141*: 350–356.
Hawker, C. (1997). *Accounts of Chem. Res. 30*: 373–382.
Hostetler et al. (1999). *Langmuir 15*: 3782–3789.
Hotz and Meier (1998). *Langmuir 14* 1031–1036.
Hu et al. (1995). *J. Appl. Polym. Sci. 58*: 375–384.
Huang and Wirth (1997). *Anal. Chem. 69*: 4577–4580.
Huang and Wirth (1999). *Macromolecules 32*: 1694–1696.
Huang et al. (1998) *Anal. Chem. 70*: 4023–4029.
Husemann et al. (2000). *J. Am. Chem. Soc. 122*: 1844–1845.
Jenekhe and Chen (1998). *Science 279*: 1903–1907.
Jordan et al. (1997). *Anal. Chem. 69*: 4939–4947.
Kato et al. (1995). *Macromolecules 28*: 1721–1723.
Kawahashi and Matijevic (1990). *J. of Coll. and Interface Sci. 138*: 534–542.
Kawahashi and Matijevic (1991). *J. of Coll. and Interface Sci. 143*: 103–110.
Krug et al. (1999). *J. Am. Chem. Soc. 121*: 9208–9214.
Lahiri et al. (1999). *Anal. Chem. 71*: 777–790.
Lee et Al. (1999). *J. Microencapsulation 16*: 715–729.
Liu and Wilcox (1995). *Mat. Res. Soc. Symp. Proc. 372*: 231–237.
Lyon et al. (1998). *Anal. Chem. 70*: 5177–5183.
Lyon et al. (1999). *Sensors and Actuators B, Chem. 54*: 118–124.
Mandal et al. (2000). *Chem. Mater. 12*: 3481–3487.
Marinakos et al. (1998). *Chem. Mater. 10*: 1214–1219.
Marinakos et al. (1999). *J. Am. Chem. Soc. 121*: 8518–8522.
Martin and Parthasarathy (1995). *Adv. Mater. 7*: 487–488.
McDonald et al. (2000). *Macromolecules 33*: 1593–1605.
Michael et al. (1998). *Anal. Chem. 70*: 1242–1248.
Morris et al. (1999). *Science 284*: 622–624.
Motesharei and Myles (1998). *J. Am. Chem. Soc. 120*: 7328–7336.
Mucic et al. (1998). *J. Am. Chem. Soc. 120*: 12674–12675.
Okubo et al. (1994). *Colloid. Polym. Sci. 272*: 270–275.
Ottewill et al. (1996). *Colloid. Polym. Sci. 274*: 763–771.
Ottewill et al. (1997). *Colloid Polym. Sci. 275*: 274–283.
Park and Kim (1998). *Biosensors and Bioelectronics 13*: 1091–1097.
Patel et al. (1997). *Langmuir 13*: 6485–6490.
Patten and Matyjaszewski (1999). *Acc. Chem. Res. 32*: 895–903.
Porter et al. (1998). *Langmuir 14*: 7378–7386.
Reynolds et al. (2000). *J. Am. Chem. Soc. 122*: 8940–8945.
Rigney et al. (1989). *J. Chromatogr. 484*: 273–291.
Schierbaum et al. (1994). *Science 265*: 1413–1415.
Schlenoff et al. (1995). *J. Am. Chem. Soc. 117*: 12528–12536.
Scott et al. (1997). *Anal. Chem. 69*: 2636–2639.
Segall et al. (1995). *J. Appl. Polym. Sci. 58*: 385–399.
Serizawa et al. (2000). *Macromolecules 33*: 1759–1764.
Sondi et al. (2000). *Langmuir 16*: 9031–9034.
Storhoff et al. (1998). *J. Am. Chem. Soc. 120*: 1959–1964.
Thurmond et al. (1997). *J. Am. Chem. Soc. 119*: 6656–6665.
Turkevich et al. (1951). *Discuss. Faraday Soc. 11*: 55–75.
Velev et al. (1996). *Langmuir 12*: 2374–2384.
Velev et al. (1996). *Langmuir 12*: 2385–2391.
Von Werne and Patten (1999). *J. Am. Chem. Soc. 121*: 7409–7410.
Wang and Matyjaszewski (1995). *J. Am. Chem. Soc. 117*: 5614–5615.
Wang and Matyjaszewski (1995). *Macromolecules 28*: 7901–7910.
Weisbecker et al. (1996). *Langmuir 12*: 3763–3772.
Wendland and Zimmerman (1999). *J. Am. Chem. Soc. 121*: 1389–1390.
Westcott et al. (1999). *Chemical Physics Letters 300*: 651–655.
Yang and Ranby (1996). *Macromolecules 29*: 3308–3310.
Segall et al. (1995). *J. of Appl. Polymer Sci. 55*: 401–417.
International Search Report for PCT/US 01/51278, mailed Feb. 5, 2003.
Schirrer, et al. (1997). Poly Eng Sci 37: 1748–1760.

* cited by examiner

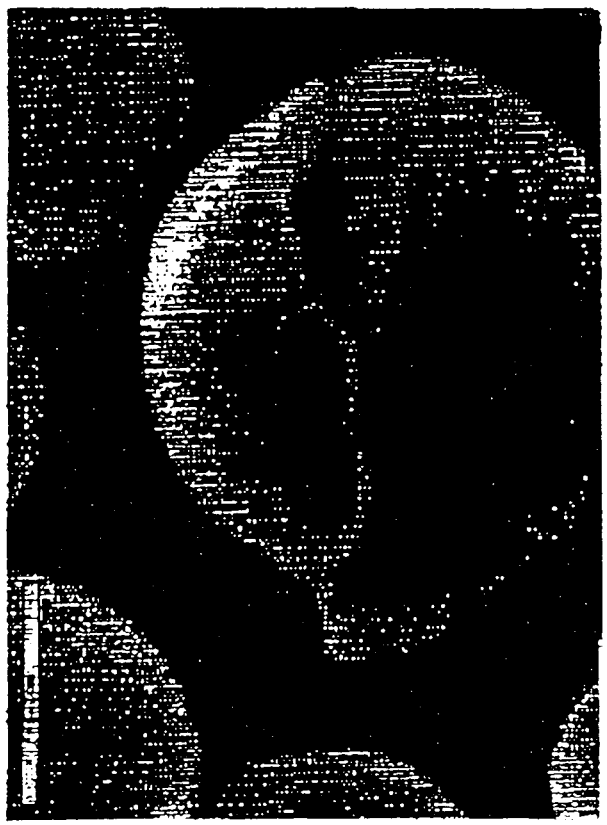
Fig. 6B — Broken hollow microspheres
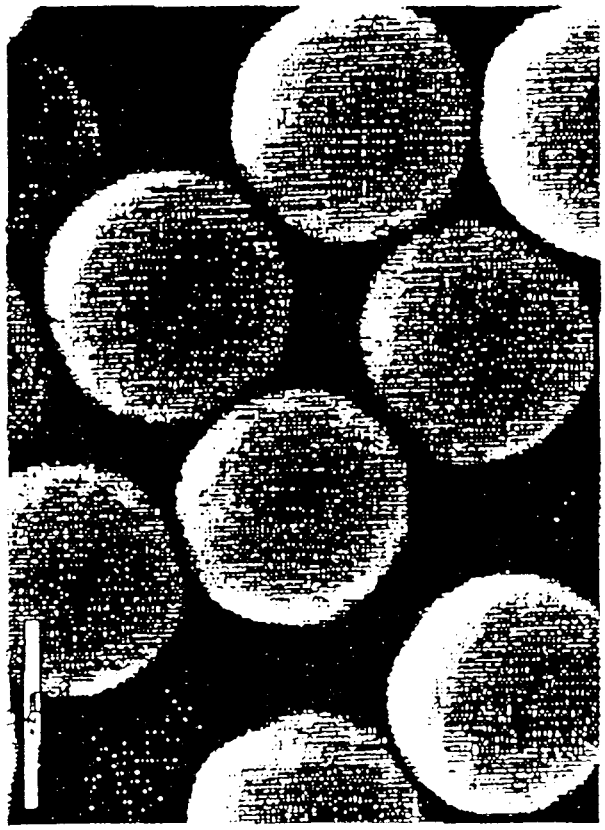
Fig. 6A — Intact hollow microspheres

Fig. 13 A-D

POLYMERIC MICROSPHERES

This application claims priority to U.S. provisional application No. 60/243,104 Oct. 25, 2000, the entire contents of which is hereby incorporated by reference.

STATEMENT TO AS FEDERALLY-SPONSORED RESEARCH

This invention was made with government support under grant number GM48142 awarded by the National Institutes of Health, grant number DE-AC05–000R22725 awarded by the Department of Energy, and DAAK60–97K-9502 awarded by the U.S. Army. The U.S. government has certain rights in the invention.

BACKGROUND OF THE INVENTION

The invention relates to microsphere particles.

Hollow microsphere particles have a wide variety industrial and biomedical uses. However, the formation of uniform and regular shell structures, as well as control over the shell thickness, is difficult to achieve using present methods, thereby restricting the uses of such particles.

SUMMARY OF THE INVENTION

The invention features hollow microspheres and core-shell microsphere compositions with consistent shell thickness using methods, which allow controlled formation of a polymeric shell. The thickness of the polymeric shell preferably varies less than 10%, more preferably less than 5%, more preferably, less than 1%, and most preferably less than 0.5%. The variability in the thickness of the polymeric shell is determined by measuring the thickness at two or more points on the microsphere and calculating % divergence.

Shell thickness is controlled by the length of polymerization and is varied to provide microspheres for divergent applications such as drug delivery or synthetic pigment preparation. Duration of the polymerization step is directly proportionate to the length of the polymer chains, and thus, shell thickness. Shell thickness is in the range of 100–1000 nm. In preferred embodiments, the shell thickness is in the range of 150–250 nm. Alternatively, the shell thickness is in the range of 350–450 nm or in the range of 550–650 nm. Preferably, the microsphere is substantially devoid of silica. For example, the microsphere contains less than 10%, more preferably less than 5%, more preferably, less than 1% silica by weight.

The microspheres contain pores. A pore is a void in the polymeric shell through which a composition may gain access to the hollow portion of the microsphere. The microspheres have a certain porosity, and the porosity is varied depending on the size and composition of the substrate used to make the sphere. Pore size is varied depending on the size and nature of the composition to be loaded into the hollow center of the sphere as well as by changing the amount of crosslinking agent added during polymerization. For example, the addition of increasing amounts of a crosslinking agent produces microspheres with decreasing pore size. Pore size is also affected by the addition of a foaming agent, i.e., addition of a foaming agent during production of the shell increases pore size. For example, a pore has a diameter in the range of 10–500 nm.

Microspheres are useful as synthetic pigments, drug delivery vehicles, and protecting agents. For example, the microspheres are used in place of titanium dioxide, i.e., as a synthetic pigment, because an empty microsphere in solution appears white. Organic dyes are encapsulated in a hollow microsphere to produce a synthetic pigment of a desired color. Empty or dye-encapsulated microspheres have several advantages over standard titanium dioxide-based paints or dyes, e.g., improved color clarity or trueness.

The microsphere is also useful as protecting agent. For example, a light-sensitive compound (e.g., a photo-bleachable dye) is loaded into a hollow microsphere to protect its degradation from exposure to light or chemicals prior to use. The compound is released from protection by disrupting the microsphere, e.g., by crushing the sphere or contacting the sphere with a solvent.

In addition to industrial applications, microspheres are used as delivery vehicles for therapeutic agents such as polypeptides, antibodies, enzymes, small molecule drugs, or nucleic acids.

The nature of the polymeric shell is varied to accommodate various uses of the hollow microspheres. The microsphere shell typically contains styrene, methacrylate, or any polymer with a high glass-transition temperature ($T_g$). The shell contains a polymer resulting from the polymerization of one or more monomers selected from the group consisting of acrylonitrile, styrene, benzyl methacrylate, phenyl methacrylate, ethyl methacrylate, divinyl benzene, 2-hydroxyethyl methacrylate, cyclohexyl methacrylate, p-methyl styrene, acrylamide, methacrylamide, methacrylonitrile, hydroxypropyl methacrylate, methoxy styrene, N-acrylylglycinamide, and N-methacrylylglycinamide. Alternatively, the shell contains a co-polymer (random or block) selected from the group consisting of styrene-PMMA, benzyl methacrylate-PMMA, styrene-PHEMA, styrene-PEMA, styrene-methacrylate, and styrene-butylacrylate. The strength and durability of the polymeric shell is increased by crosslinking polymer chains.

The invention also includes methods of making hollow microspheres by providing a substrate containing a plurality of hydroxyl groups and attaching an initiator agent to the hydroxyl groups to form attached initiator agents. Any solid substrate, which is characterized as containing hydroxyl groups on its surface and is dissolvable (following polymerization of the shell) is suitable. For example, the substrate is silica, alumina, mica, or a clay composition. Alternatively, the substrate is a crystal, which has been coated with a silica. The initiator agents react with a polymerizable unit under polymerization conditions to form a polymer shell over the substrate. The polymerization is confined to a surface of the substrate. A polymer chain is initiated at the initiator agent and is extended away from the substrate during polymerization. To remove the substrate from the polymeric shell (to yield a hollow microsphere), the substrate is contacted with an etching agent for a time sufficient to allow for elimination of the substrate from the polymeric shell. An etching agent is a composition which removes a solid substrate from the center of a polymer-coated substrate, leaving a polymeric shell. Preferably, at least 85% of the substrate, more preferably 95%, more preferably 99%, and most preferably 100% of the substrate is removed from the core of the sphere. Etching agents include bases or acids, e.g., hydrochloric acid (HCl), hydrogen fluoride (HF), sulfuric acid ($H_2SO_4$), sodium hydroxide (NaOH), potassium hydroxide (KOH). Alternatively, the substrate is metal, and the etching agent is an oxidizing or reducing agent. For example, a silica substrate or mica is removed by etching with HF, and an alumina or clay substrate is removed by etching with KOH. Optionally, the method includes a step of exposing the polymer shell to a crosslinking agent.

The polymerizable unit is a monomer selected from the group consisting of acrylonitrile, styrene, benzyl methacrylate, phenyl methacrylate, ethyl methacrylate, divinyl benzene, 2-hydroxyethyl methacrylate, cyclohexyl methacrylate, p-methyl styrene, acrylamide, methacrylamide, methacrylonitrile, hydroxypropyl methacrylate, methoxy styrene, N-acrylylglycinamide, and N-methacrylylglycinamide or a co-polymer selected from the group consisting of styrene-PMMA, benzyl methacrylate-PMMA, styrene-PHEMA, styrene-PEMA, styrene-methacrylate, and styrene-butylacrylate. Thickness of the developing polymeric shell is controlled by the length of polymerization.

The invention also includes a core-shell composition. A core-shell composition is a composition, which contains at least two structural domains. For example, the core domain is encased in the shell domain, and the shell domain is characterized as having different physical and chemical properties than the core. The core portion contains a first compound, and the shell contains a second compound (which is not present in the core portion). The core and shell differ by the presence or absence of at least one compound. A method for preparing a core-shell composite includes the following steps: providing a microsphere substrate; contacting the microsphere substrate with a polymer nanosphere to yield a colloidal assembly; and heating the assembly to yield a core-shell composite.

An alternative method for preparing a hollow microsphere includes the following steps: providing a microsphere substrate; contacting the microsphere substrate with a polymer nanosphere to yield a colloidal assembly; heating the assembly to yield a core-shell composite; and exposing the composite to an etching agent for a time sufficient to allow for removal of a core composition, e.g., silica, from the shell polymer composition to form a hollow microsphere.

A colloidal assemby is an organized structure of two or more particle types. For example, the assembly is organized such that the nanospheres are assembled onto the surface of a microsphere. Preferably, the microsphere is 1–100 μm in diameter; more preferably, the microsphere is less than 75 μm in diameter; more preferably, the microsphere is less than 50 μm in diameter; and even more preferably the microsphere is less than 25 μm in diameter. For example, the microsphere is 3–10 μm in diameter. The nanosphere is 1–1000 nm in diameter. Preferably, the nanosphere is less than 500 nm; more preferably, the nanosphere is less than 250 nm. For example, the nanosphere is 100–200 nm in diameter.

The nanospheres and/or microspheres are optionally modified to contain a reactive substituent. Preferably, the microsphere and nanosphere contain different substituents, which associate, bind, or react with one another. For example, the nanosphere contains an amine-modified polymer, e.g., an amine-modified polystyrene (PS), and the microsphere comprises an aldehyde-modified composition, e.g., glutaraldehyde-activated silica. The microsphere substrate contains silica, alumina, mica, or clay. In another example, the nanosphere contains avidin and the microsphere contains biotin, or the nanosphere contains biotin and the microsphere contains avidin. The nanosphere may contain one type of polymer or a mixture of polymers. For example, the nanosphere contains PS, PMMA, or both. The microspheres are optionally contacted with a mixture of different nanospheres, e.g., a mixture of PS nanospheres and PMMA nanospheres, to yield a composite polymer shell. The ratio of different polymer nanospheres is varied to achieve a desired effect, e.g., strength or porosity. For example, the ratio of PS:PMMA is 50:50, 100:1, 10:1, 5:1, or 2:1.

The colloidal assembly is heated to a temperature greater than the $T_g$ of the polymer nanosphere to melt the polymer nanospheres. The polymer flows over the microsphere surface resulting in an essentially uniform coating, i.e., the thickness of the polymer shell varies less than 10% over its entire surface. For example, the colloidal assembly is heated to at least 100° C. To melt PS and/or PMMA nanospheres, the colloidal assembly is heated to 170–180° C.

Other features and advantages of the invention will be apparent from the following description of the preferred embodiments thereof, and from the claims.

BRIEF DESCRIPTION OF THE DRAWINGS

FIG. 1A is a micrograph of silanized silica microspheres, and FIG. 1B is a micrograph of the same microspheres after coating with poly(benzyl methacrylate) by controlled/living radical polymerization for 14 h.

FIG. 2A is a scanning electron micrograph of etched microspheres, and FIG. 2B shows the microspheres dispersed in water to allow visualization of individual particles.

FIG. 4A, 3.5 h polymerization; FIG. 4B, 6.5 h polymerization; and FIG. 4C, 14 h polymerization.

FIGS. 6A–B are scanning electron micrographs of hollow shell cross-linked PBzMA microspheres. FIG. 6A shows intact hollow microspheres, and FIG. 6B shows broken hollow microspheres.

FIG. 13A shows 3.0 μm mean diameter glutaraldehyde coated silica assembled with 100 nm mean diameter amino-functionalized polystyrene particles. FIG. 13B shows 5.0 µm mean diameter glutaraldehyde coated silica assembled with 200 nm mean diameter amino polystyrene nanoparticles. FIG. 13C shows 5.0 µm mean diameter avidin-coated silica assembled with 100 nm mean diameter biotin-coated polystyrene nanoparticles. FIG. 13D shows polystyrene film coated silica particles, which result from heating microspheres identical to those shown in FIG. 13A to 170–180° C. in ethylene glycol.

FIG. 14 is a tapping mode scanning force microscopy (SFM) scan of the surface of the composite produced when 200 nm PS nanospheres are assembled on 5 µm diameter silica.

FIG. 17A shows a comparison of the spectra in the range of 650 cm–1 to 780 cm–1. Bands at 750 cm–1 and 697 cm–1 correspond to polystyrene benzene C-H stetching and ring bending vibrations.

DETAILED DESCRIPTION

Hollow polymer microspheres were prepared by coating silica microsphere templates with poly(benzyl methacrylate) using surface initiated controlled/living radical polymerization and subsequently removing the core by chemical etching. Shell thickness was controlled by varying the polymerization time. Scanning electron microscopy was used to characterize the products and demonstrate that the polymer microspheres were hollow. FTIR spectroscopy showed that the silica cores were completely removed by etching.

Figure 3:
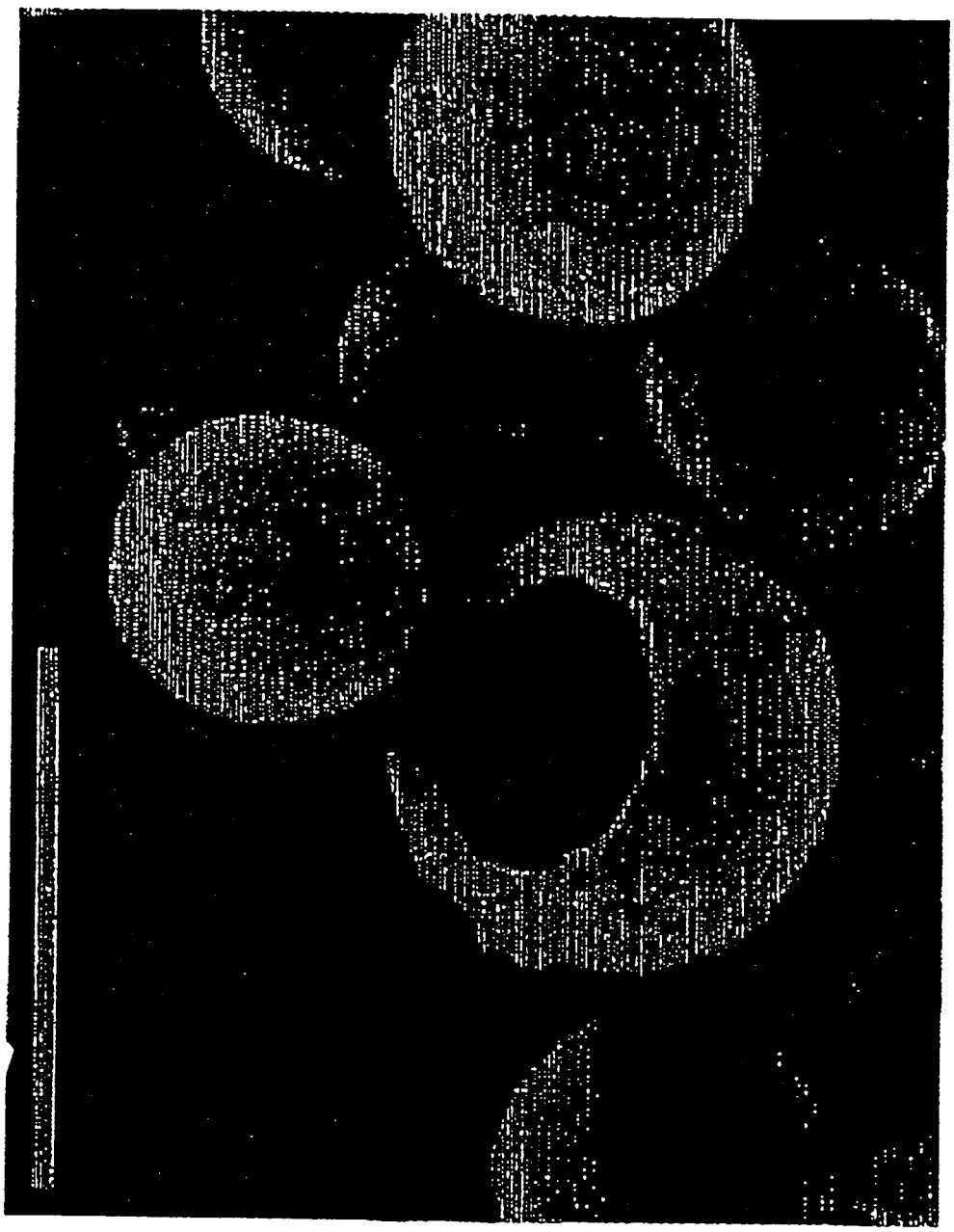
FIG. 3 is a scanning electron micrograph of the hollow polymeric microspheres obtained by crushing the hollow spheres by applying physical pressure after freezing in liquid nitrogen. Both broken and intact polymer spheres are seen.
Figure 9:
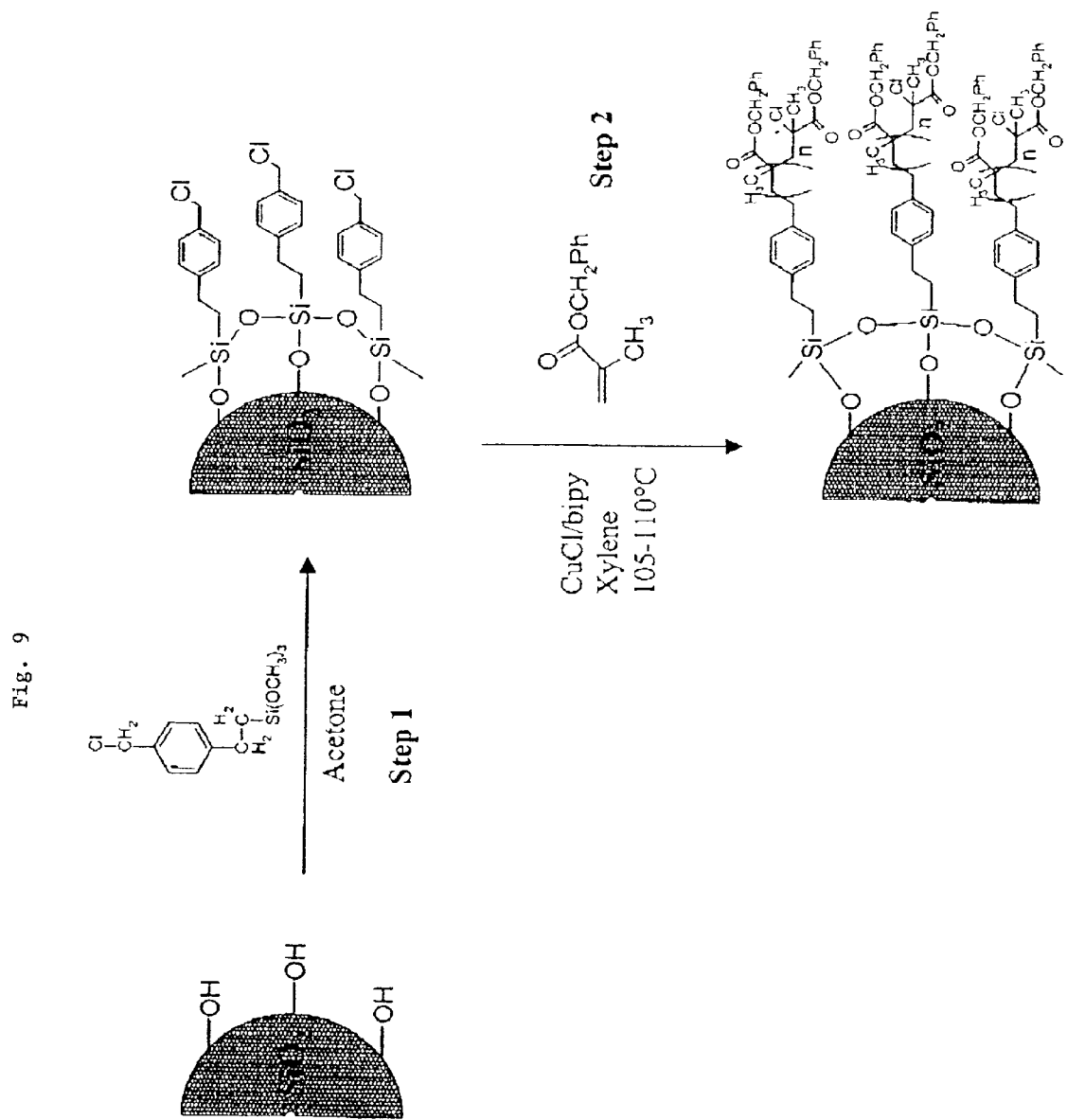
FIG. 9 is a diagram showing a polymerization step for coating silica particles.

Surface Confined Living Radical Polymerization: A New Method for Preparing Hollow Polymer Microspheres on Silica Templates Uniform hollow polymeric microspheres were made by using surface confined living radical polymerization. Using the silica microsphere as a sacrificial core, hollow microspheres were produced following core dissolution. First, a controlled/living polymerization was conducted using an initiator attached to the surface of silica microparticles to initiate atom transfer radical polymerization (ATRP). This procedure yielded core-shell microparticles with a silica core and an outer layer of covalently attached, well-defined, uniform thickness polymers. The silica cores were subsequently dissolved, resulting in hollow polymeric microspheres. Silica microspheres were coated with polymer in two steps (FIG. 9). For example, first a benzyl chloride monolayer was prepared by silanization of silica microspheres. In the second step, surface-modified silica microspheres were heated in presence of copper halide, complexing agent (dipyridyl) and benzyl methacrylate monomer in xylene at high temperature to prepare uniformly coated microspheres. Polymer coated silica microspheres were then immersed in aqueous HF solution to yield uniform hollow poly(benzyl methacrylate) (PBzMA) microspheres. In order to confirm that the microspheres are hollow, the microspheres were first frozen in liquid nitrogen and then crushed between two glass plates. FIG. 3 shows a SEM image of intact and broken hollow polymer microspheres.

The process by which hollow polymeric microspheres are made differs significantly from methods known in the art. The method presented herein for preparing uniform hollow polymeric beads utilizes surface confined living radical polymerization technique on silica templates.

Earlier processes for making hollow polymer latex particles include one developed by Rohm and Haas. This earlier process involved making structured particles with a carboxylated core polymer and one or more outer shells. The ionization of the carboxylated core with base expands the core by osmotic swelling to produce hollow polymer particles. Another method involved an emulsion polymerization of styrene containing a small amount of vinyl carboxylic acid in the presence of a hydrocarbon, surfactant, and a water miscible alcohol. These processes are complex and involve several steps employing different chemistries. Other methods involve the synthesis of hollow nanoscopic polypyrrole particles to employ gold nanoparticles as a template from which to grow the polymer shell, followed by dissolution of the template. The methods of the invention offer several advantages over earlier know methods in that the present process yields microspheres with relative uniformity of shell thickness. Another advantage is that the shell thickness is reliably and consistently controllable. In contrast, formation of uniform and regular shell structures surrounding the particles, as well as control over the shell thickness, has been difficult to achieve using the earlier methods, because polymerization is not restricted to the surface of the templates.

The surface confined living radical polymerization method presented herein is simple, flexible and enables control over the shell thickness and composition by adjusting polymerization time and monomer concentration. Unwanted solution phase polymerization is also prevented using this method. This method is applicable for preparing variety of hollow polymer microspheres. This approach may allow for the fabrication of different shapes of hollow polymeric materials produced from a variety of templates.

A wide range of monomers are used to make the shell of the hollow microsphere. Examples of monomers, which are compatible with the living polymerization procedure, are listed in Table 1.

TABLE 1

| Monomers for shell construction |
| --- |
| Acrylonitrile |
| Styrene |
| Benzyl methacrylate |
| Phenyl methacrylate |
| Ethyl methacrylate |
| Divinyl benzene |
| 2-Hydroxyethyl methacrylate |

TABLE 1-continued

Monomers for shell construction

Cyclohexyl methacrylate
p-Methyl styrene
Acrylamide
Methacrylamide
Methacrylonitrile
Hydroxypropyl methacrylate
Methoy styrene
N-Acrylylglycinamide
N-Methacrylylglycinamide Co-polymers may also be produced. A list of suitable co-polymers is provided in Table 2. Monomer designations are abbreviated as follows: PMMA, Poly(methyl methacrylate); PHEMA, Poly(hydroxyethyl methacrylate); PEMA, Poly(ethyl methacrylate).

TABLE 2

Co-polymers

Styrene-PMMA
Benzyl methacrylate-PMMA
Styrene-PHEMA
Styrene-PEMA
Styrene-Methacrylate
Styrene-Butylacrylate As is described above, a silica particle serves as a scaffold upon which the shell is built by polymerization. An initiator is attached to the surface of silica microparticles to initiate atom transfer radical polymerization (ATRP). Examples of Living Radical Initiators (which are immobilized on microsphere surfaces by silanization or some other method prior to living radical polymerization) include those listed in Table 3.

TABLE 3

Living Radical Initiators

Phenyl ethyl chloride
Phenyl ethyl bromide
Phenyl sulfonyl chloride
2-Bromoethylisobutyrate Uses for hollow microspheres Hollow polymer microspheres are a class of materials which have application in the fields of medicine and materials science. For example, the microspheres are used for product encapsulation for controlled release of drugs and dyes, protection of light sensitive compounds, enzyme encapsulations, and adhesives.

Hollow microspheres are made in a wide range of sizes (inner/outer diameter) to suit a particular application. Pore size may also be varied to order. Pore size is controlled by varying the amount of crosslinker in the polymerization mixture. Generally, the pore size of the hollow microsphere is slightly larger than the pore size of the template due to the etching process. A larger pore size is suitable for adhesive applications whereas a smaller pore size suits encapsulation of enzymes or other therapeutic agents. Spheres with a pore size of 100 nm to 500 nm (e.g., a sphere, which has a diameter of at least 1 micron sphere in which the diameter of the pore is greater than about 10% of the diameter of the sphere) are useful in the formulation of adhesives.

Synthetic Pigments

Hollow polymer nanospheres and microspheres are useful in the industrial production of paints and pigments. The microspheres are added to convention paint formulations as extenders. Hollow polymer microspheres and nanospheres (e.g., 300–500 nm outer diameter) are used in the production of synthetic pigments. Hollow polymer particles with outer diameters in the range of 1–5 microns in diameter have been produced using the methods described herein. These particles are useful in the production of synthetic pigments as well. Nanometer-scale hollow spheres are produced by performing living polymerization with 300–500 nm diameter silica templates, followed by silica etching in hydrofluoric acid.

The method described herein for preparation of hollow polymer microspheres may have several advantages over current methods for preparing synthetic pigments. Since synthetic pigments are made from hollow polymer spheres, the shell thickness and composition must be controlled in some manner. Shell thickness is correlated with the opacity of the resulting pigment. Template directed living polymerization allows the polymer shell thickness to be more accurately controlled than in other known methods. This results in better control of the opacity of the resulting pigment. Polydispersity of the polymer in the spheres also influences opacity. By using living polymerization methods, polydispersity is also under better control and more consistent than in other methods. Polydispersity also influences the uniformity of the hollow microsphere surface.

Material Encapsulation/Drug Delivery

Hollow polymer microspheres also have application in the fields of materials encapsulation and drug delivery. Drugs such as tranilast or ibuprofen are encapsulated in polymeric microspheres. The spheres are used to slowly release drug over time in the digestive tract. Biocompatible hydrogels such as polyacrylamide-chitosan are useful for sustained antibiotic release. For example, microspheres with a core size of approximately 3 micrometers are used for drug delivery.

Microspheres produced by living polymerization are more advantageous for drug delivery applications because of the consistency in shell thickness and porosity. In contrast, the shell thickness of the microspheres produced by existing technology cannot be controlled during the polymerization. Being able to control the shell thickness and therefore the rate of drug release from the microspheres is a significant advantage of the microspheres of the invention.

Figure 11:
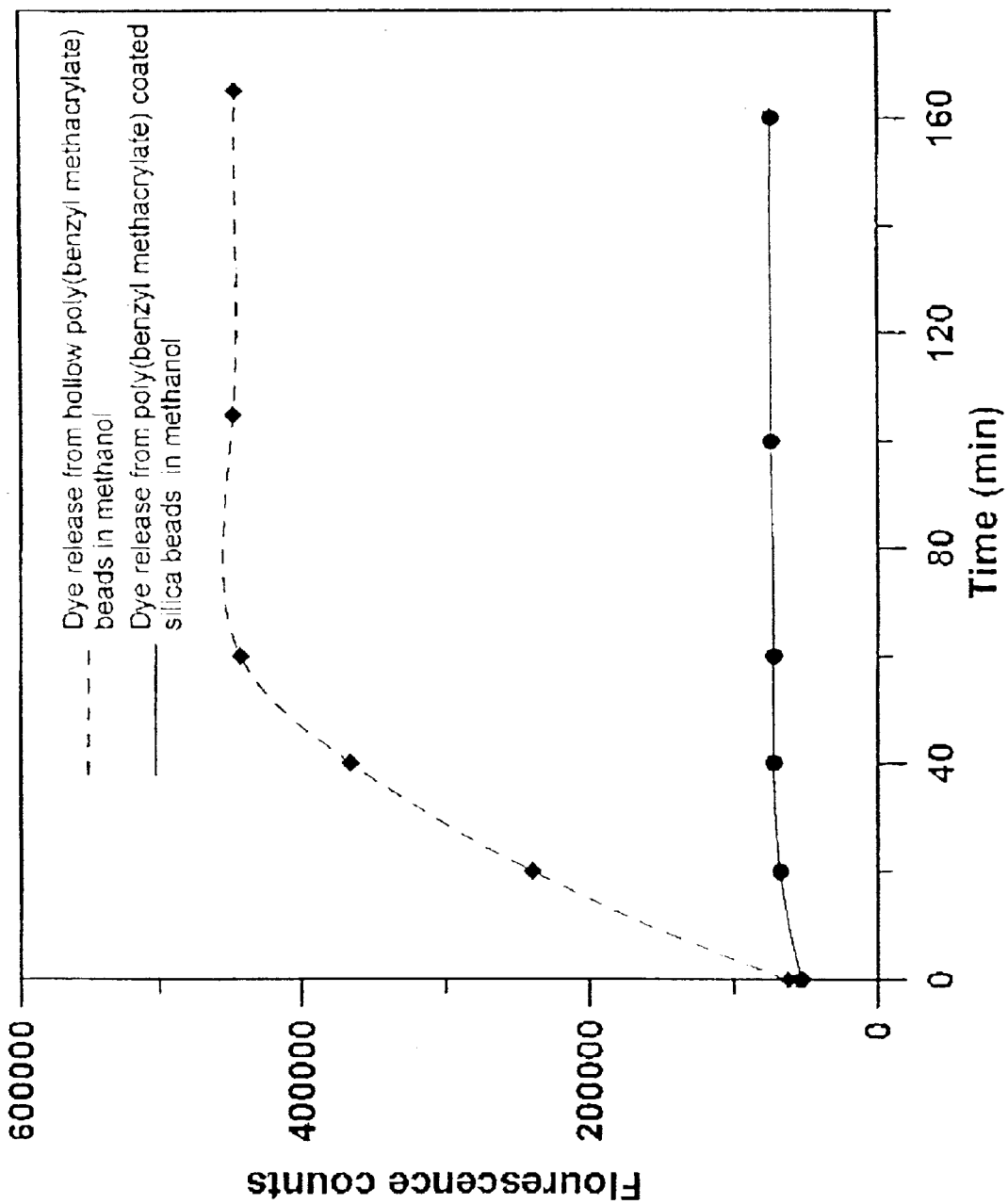
FIG. 11 is a line graph showing release of fluoroscein from hollow microspheres (dashed line) compared to release from coated beads over time.

Studies on encapsulation and release of test agents, e.g., a dye, from hollow microspheres were carried out as follows. Crosslinked hollow poly(benzyl methacrylate) or PBzMA coated silica (approximately 1 mg) beads were soaked with fluorescein in a methanol solution overnight. Excess fluorescein was removed by centrifugation (1000 rpm), followed by a wash with methanol. The dye-loaded beads were immersed in 0.5 ml methanol. Release of the dye from hollow microspheres was monitored by measuring the increase in fluorescence of the surrounding solution as a function of time. The data shown in FIG. 11 indicate that hollow microspheres or beads (dashed line) are effectively loaded with a composition of interest and that the composition is released from the hollow microspheres into the surrounding environment in a time-dependent manner. In contrast, the composition is not loaded (and therefore, not released) from coated solid beads (solid line) under the same conditions.

Microspheres produced for delivery of therapeutic products are washed with water or a physiologically-compatible buffer (e.g., phosphate-buffered saline) following the etching procedure to remove the silica template and residual etching agent. The microspheres are then contacted with a therapeutic agent in solution phase. The microspheres are loaded with the agent by diffusion.

Block co-polymer hollow microspheres may be produced using the living polymerization method. The composition of the blocks can be tailored for particular drug delivery applications.

Protecting Agents

Hollow polymer microspheres are used as protecting agents to stabilize materials from exposure to light, solvents or other exposures to which they may be sensitive. For example, a sensitive composition is loaded into the microspheres. The composition is protected from light or exposure to other damaging agents until the microsphere is physically or chemically disrupted and the compositions is released from the microsphere.

Hollow microspheres are also used as coatings. The polymer used to make the polymeric shell of the hollow microsphere is tailored to the application desired. For example, acrylate or methacrylate polymers are suitable for most coating applications. Such microspheres are useful as sunscreen compositions. The microspheres are used alone or in combination with standard sunscreen compositions.

Hollow microsphere coatings are applied to paper or photographs to protect them from light-mediated aging.

Production of Hollow Microspheres

Figure 10:
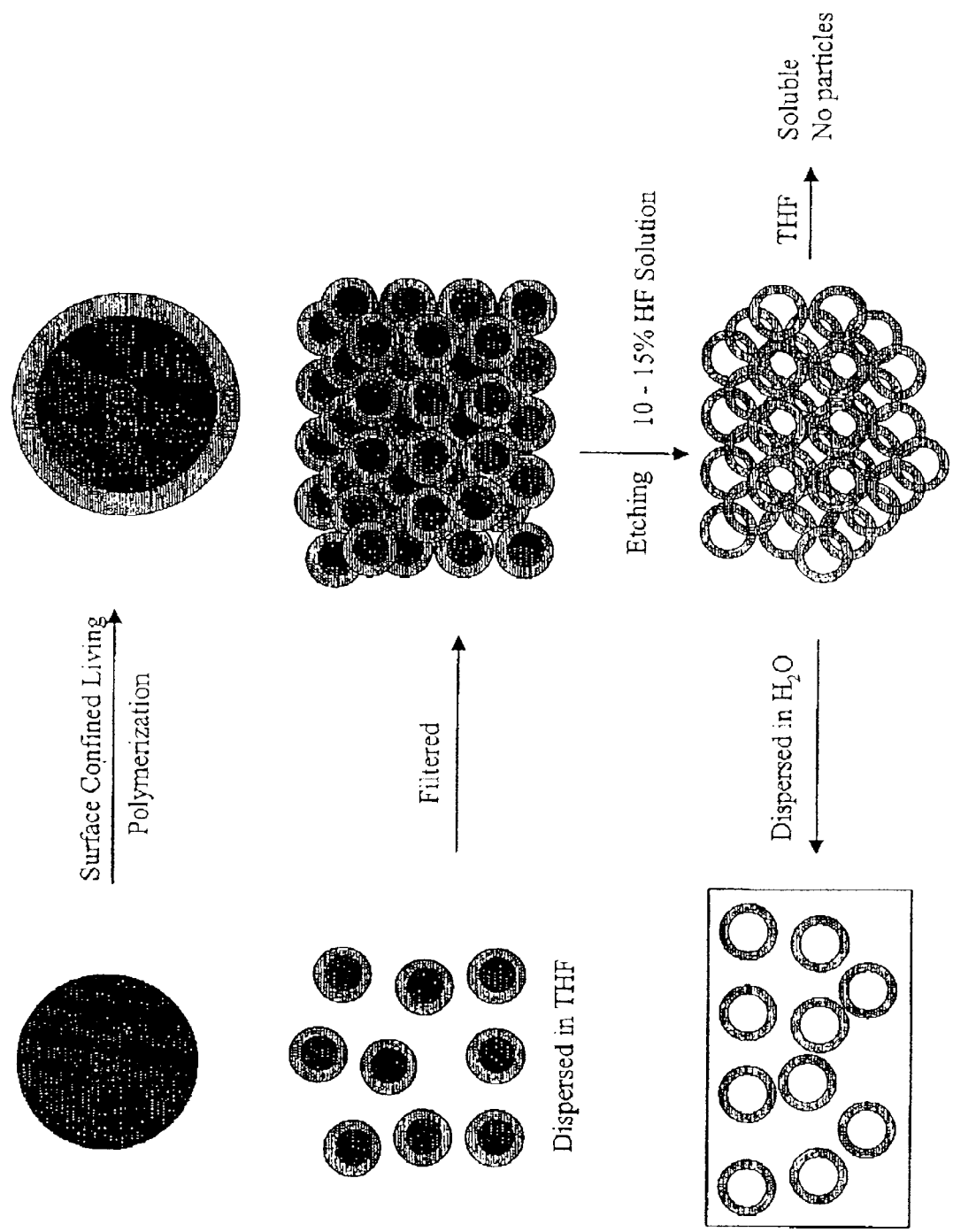
FIG. 10 is a diagram showing a method for making hollow microspheres.

The process for making uniform hollow polymeric microspheres utilizes surface confined living radical polymerization. Using the silica microsphere as a sacrificial core, hollow microspheres are produced following core dissolution. First, a controlled/living polymerization is conducted using an initiator attached to the surface of silica microparticles to initiate atom transfer radical polymerization (ATRP). This procedure yields core-shell microparticles with a silica core and an outer layer of covalently attached, well-defined uniform thickness poly(benzyl methacrylate) (FIG. 9). The silica cores are subsequently dissolved, resulting in hollow polymeric microspheres (FIG. 10). Surface-initiated living polymerization is a polymerization process in which control of molecular weight is controlled by adjusting the monomer concentration and termination reactions are substantially eliminated. Polydispersity is thus lowered, enabling fine control of shell thickness, i.e., the shell surfaces are more uniform. Shell thickness and variations in shell thickness between two or more locations of the sphere are measured using methods known in the art.

In comparison to standard solution or bulk living polymerization, surface-initiated living radical polymerization has several advantages. The growing radicals generated on the surface are not easily terminated by bimolecular reactions due to limitations of the solid surface on which the polymer chains are chemically attached, the low free radical concentration and the low mobility. By using a controlled living polymerization procedure to covalently attach polymer chains to microsphere surfaces, one can control the thickness and uniformity of the coated polymer film. Unwanted solution phase polymerization is also prevented using this method. An additional benefit is the ability to prepare block copolymers by the sequential activation of the dormant chain end in the presence of different monomers. Although grafting of polymers on flat and porous silica surfaces by using living radical polymerization (von Werne et al., 1999, J. Am. Chem. Soc. 121:7409–7410) has been described, the procedure for making uniform hollow polymeric beads by using the living radical polymerization technique on a silica microsphere template is completely new. The process of von Werne et al. is a method of making a composite film by grafting flat and porous silica surfaces particles using living radical polymerization. Rather than producing microspheres, the method of von Werne et al. yields a hexagonally-ordered film with embedded silica nanoparticles. In contrast, the inventive method yields hollow microspheres with shells of consistent thickness.

Reagents

Benzyl methacrylate, ethylene glycol dimethacrylate, 2,2'-dipyridyl (99%) and copper (I) chloride were purchased from Aldrich Chemical Co (Milwaukee, Wis.). Luna porous silica beads (~3 $\mu$m) were purchased from Phenomenex (Torrance, Calif.) and Bangs silica beads (~3.1 $\mu$m) were from Bangs Laboratories, Inc. (Fishers, Ind.). ((Chloromethyl)-phenylethyl) trimethoxysilane (CTMS) was obtained from Gelest, Inc (Tullytown, Pa.). High performance liquid chromatography (HPLC) grade solvents were used in both the reaction and washing steps. All the reagents were used without further purification.

Preparation of Poly(benzyl methacrylate)-coated Silica Microspheres

The reactions for bead coating consisted of two steps, which are schematically shown in FIG. 9. The silica particles were first cleaned with acetone several times to remove potential impurities. A benzyl chloride monolayer was prepared by silanization of silica microspheres. A mixture of 0.9 ml of acetone and 0.1 ml of CTMS were added to 6–7 mg of purified silica microspheres in a 1.5 ml polypropylene microcentrifuge tube. The bead suspension was shaken at room temperature for 2 h in the dark. After silanization, the silica beads were separated from the suspension by centrifugation, washed with acetone to remove unreacted silane coupling agent and then cured at room temperature overnight in the dark.

In the second step, the living radical polymerization was performed. A 4 ml glass vial was charged with 6–7 mg of the silanized silica microspheres and 0.75 ml of dry p-xylene. Dry argon gas was bubbled through the mixture for 15 min to remove oxygen from the polymerization system. After the removal of oxygen, 0.0067 g (0.068 mmol) of CuCl, 0.0316 g (0.21 mmol) of 2,2'-dipyridyl and 0.75 ml of benzyl methacrylate were added to the same reaction mixture. The vial was then sealed with a high temperature silicone rubber septum and argon was bubbled through the mixture for another 20 min. to ensure that oxygen was removed completely. The mixture was sonicated for 1 min to accelerate dissolution into xylene. The reaction was heated with constant stirring (with a magnetic stir bar) at 105–110° C. using a silicone oil bath. Polymerization time was varied from 1 to 14 h to produce polymer shells with different thicknesses. After polymerization, the coated microspheres were separated from the suspension by centrifugation, and then washed several times by centrifuging/resuspending in THF and methanol. Cross-linked polymer shells were prepared by adding 10% ethylene glycol dimethacrylate (with respect to benzyl methacrylate monomer) into the above mixture. The rest of the procedures were the same as those for linear polymerization.

Procedure for Making Hollow Polymeric Microspheres

The synthesis of hollow polymeric microspheres is schematically represented in FIG. 10. Briefly, PBzMA coated silica particles were first suspended in tetrahydrofuran (THF). The bead suspension was filtered through a 0.5 micron pore size Fluopore membrane (Millipore Corporation, Bedford, Mass.). A thin pellet of coated microspheres was formed on the top of the membrane. The product was dried in an oven at 60° C. for 2 h. A 10% aqueous hydrogen fluoride (HF) solution was prepared by diluting 50% HF with ultra-pure water. The membrane containing the pellet was placed in a small polystyrene Petri dish and then 3.25 ml of 10% HF solution was added to immerse the pellet. The reaction was allowed to continue for 3 h at room temperature to etch the silica cores completely. The film was then withdrawn, dipped in ultra-pure water which was replaced with fresh water 4–5 times to remove all the unreacted HF. Finally, the pellet was redispersed in water to obtain the individual hollow PBzMA microspheres.

Fourier Transform Infra Red (FTIR) Spectroscopy

FTIR (Nicolet Magna-760, Nicolet Instrument Corporation, Madison, Wis.) spectroscopy was used to identify a polymer on the bead surface and also to ensure that silica was removed from the inside of the hollow polymeric bead. Spectra were obtained at a resolution of 2 $cm^{-1}$ and averages of 64–100 spectra/scans (for enhanced signal) were obtained in the wavenumber range 400–4000 $cm^{-1}$. Spectra of the pure silica and polymer coated silica were recorded from KBr pellets, prepared by mixing the microspheres with KBr in 1:100(wt/wt) ratio. FTIR spectra for the pure PBzMA and the hollow polymer beads were obtained at room temperature by casting a THF solution on KBr pellets. FTIR spectra of the shell cross-linked hollow PBzMA microspheres were also measured from KBr pellets, prepared by the same procedure described above.

Scanning Electron Microscopy (SEM)

SEM was performed using a JEOL SM 840 scanning electron microscope (JEOL, Peabody, Mass.) at an accelerating voltage of 25 kV. Samples were mounted on an aluminium stub and sputter coated with gold to minimize charging. To obtain more information about the internal structure of the hollow microspheres, dry etched polymer particles were sheared between two glass slides after freezing in liquid nitrogen to obtain cracked beads using standard procedures. This technique allows determination of the polymer shell thickness.

Atomic Force Microscopy (AFM)

Surfaces of hollow polymer microspheres were imaged using a Digital Instruments Nanoscope IIIa scanning probe microscope. (Digital Instruments Inc., Santa Barbara, Calif., USA). Images were acquired in Tapping mode with the Z range set at 4.0 $\mu$m. Scan size was 7.0 $\mu$m The scan rate was 0.5 Hz. Images were acquired using a diamond coated tapping mode tip (L=125 $\mu$m, $F_o$=360 kHz). Samples of hollow polymer microspheres were allowed to dry from an aqueous suspension onto a glass microscope slide prior to AFM analysis. Surface roughness analysis was performed using Digital Instruments Nanoscope software (version 4.10).

Gel Permeation Chromatography (GPC)

Molecular weights and molecular distributions were obtained on a Waters 2690 Separation Module (Waters Corporation, Milford, Mass.) connected to a Waters 410 Differential Refractometer with THF as the carrier solvent. Molecular weights were calibrated using polystyrene standards.

Characterization of Hollow Polymeric Microspheres Produced by Surface-Confined Living Radical Polymerization on Silica Templates Spherical silica particles with an average diameter of 3$\mu$ were used as a template for the synthesis of uniform hollow poly(benzyl methacrylate) microspheres. The ((chloromethyl)-phenylethyl)trimethoxysilane (CTMS) initiator was attached to the silica surface by treating the silica with CTMS in acetone. Upon curing, a covalently linked benzyl chloride monolayer is formed on the silica microsphere surface. Elemental analysis results showed that the initial silica microparticles contained <0.02% chlorine and that the CTMS-attached microparticles contained 3.15% chlorine (Galbraith Laboratories, Inc., Knoxville, Tenn.). This difference is equivalent to an average of 0.88 mmol initiator/g of silica. The grafting density of the monolayer of benzyl chloride was 2.3 $\mu$mol/m$^2$, calculated on the basis of average surface area (400 m$^2$/g, data supplied by Phenomenex) of the pure silica particles. The resulting surface modified silica particles could be redispersed in organic solvents. Scanning electron micrographs of the CTMS modified silica microparticles showed that they remain unaggregated (FIG. 1A) and were similar to the original silica microparticles, exhibiting no characteristic features. Although, benzyl chloride (—Ph—CH$_2$Cl) of CTMS is generally not an efficient initiating group for atom transfer radical polymerization compared to 1-phenylethyl chloride or bromide, it performed adequately in this case. Silica microspheres are coated with higher molecular weight PBzMA by using alternative initiators such as those listed in Table 3.

Figure 1B:
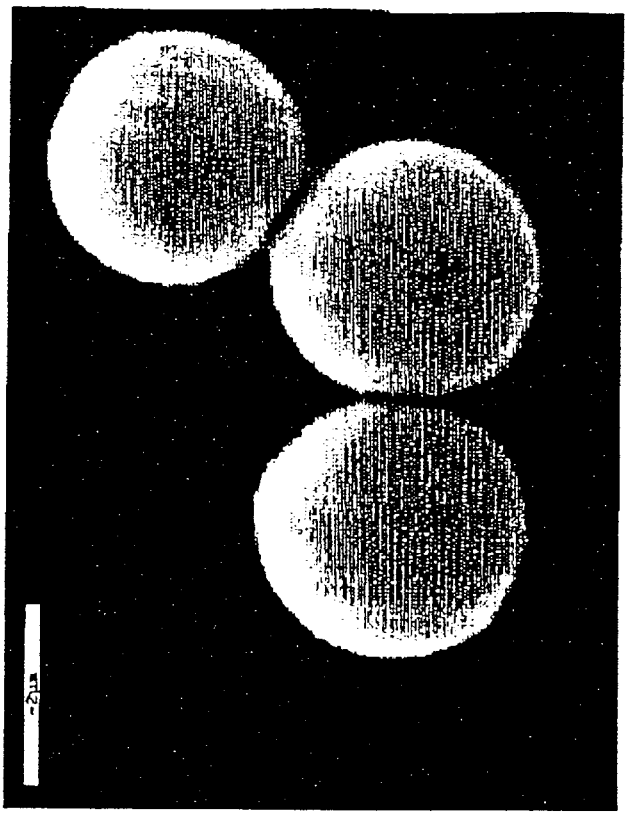
FIGS. 1A and 1B are scanning electron micrographs of hollow microspheres.

The surface modified microparticles were then used as macroinitiators for benzyl methacrylate atom transfer radical polymerization. Polymer growth was confined to the surface of initiator-modified silica microspheres. The polymer coated silica microspheres were dispersed easily in good solvents for poly(benzyl methacrylate)(PBzMA). FTIR spectra of the resulting composite particles showed bands corresponding to both poly(benzyl methacrylate) and silica. A SEM micrograph of the polymer coated silica microspheres shows that the polymer is uniformly coated over the silica surface (FIG. 1B). Tapping mode atomic force microscopy was used to obtain more detailed information about the surface topography. The AFM image of the surface of hollow polymer microspheres shows that the surface was very smooth. The root mean-square roughness (Rq) value is 8–10 nm. This value compares well with Rq values for silanized non-porous silica microspheres. ATRP forms primarily monodisperse polymer chains, with a uniform surface coating. The thickness of the polymer layer increases with increasing polymerization time at fixed monomer concentrations. Although the possibility exists that when polymer chains are densely grafted to a surface, steric crowding forces the chains to stretch away from the surface, the curvature of the silica particles may help to reduce steric crowding. Overall, the thickness of the polymer layer should be larger than the radius of gyration for the equivalent free polymer in solution.

Figure 2B:
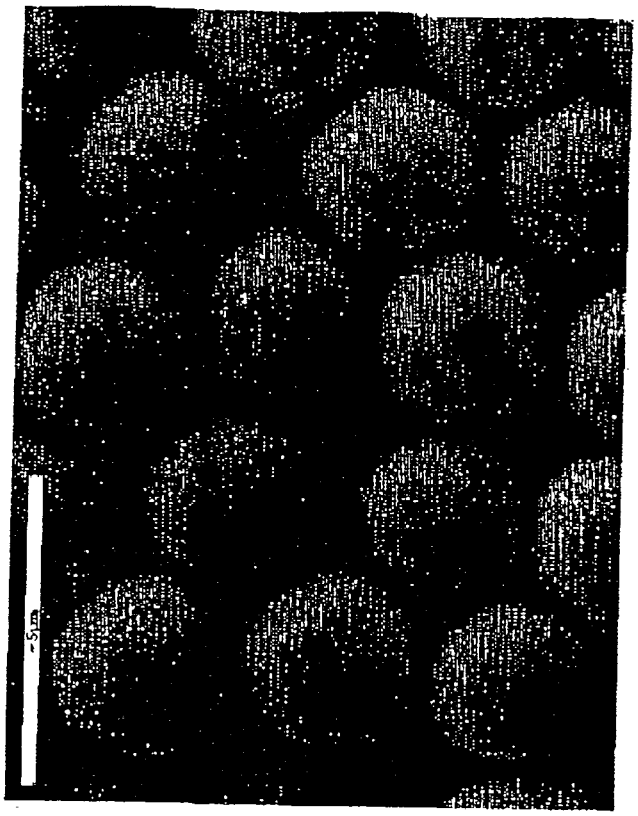
FIGS. 2A and 2B are scanning electron micrographs of the polymer microspheres after etching with HF.
Figure 2A:
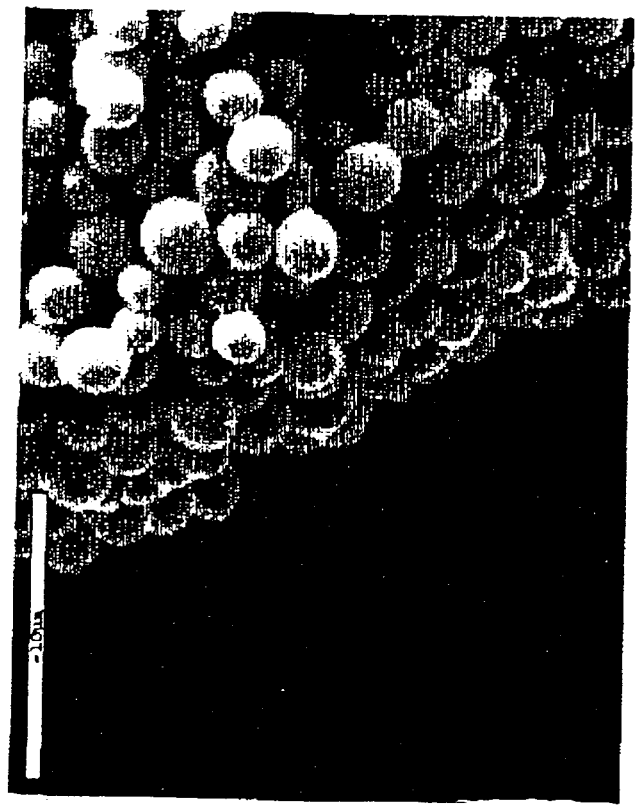

Polymer/silica particle composites were converted to hollow polymeric microspheres by immersing a pellet of the composite particles (supported by a Fluopore membrane) in an aqueous solution of HF. Silica dissolution occurs via transport of etchant through the polymer shell to the core. FIG. 2A shows the SEM micrograph of the aggregated intact hollow PBzMA microspheres after etching the silica core. Aggregated hollow polymer particles were redispersed as individual particles by sonicating a portion of the pellet in water (FIG. 2B). When the composite particles are prepared by 1 h polymerization, no hollow microspheres are obtained after HF etching. This result indicates that the polymer shell thickness was not sufficient to maintain the initial spherical structure of the silica microsphere upon core removal. The hollow microspheres are soluble in THF and other organic solvents because the polymer chains are no longer grafted to the solid silica surface. This result proves that the silica cores are completely etched by the HF solution. Shell cross-linked hollow polymer microspheres, however, are not soluble in most organic solvents. For this reason, they are useful for drug delivery or encapsulating drugs/dyes in non-aqueous solvents.

After etching the silica core, the spheres were dissolved in THF and the molecular weight of the dissolved polymer was determined by GPC. The molecular weights of three samples of cleaved surface initiated PBzMA, prepared with different polymerization times, are given in Table 4.

TABLE 4

Shell thicknesses and molecular weights of the hollow poly(benzyl methacrylate) microspheres prepared by varying polymerization time

| Polymerization time (hr) | Shell thickness (nm) | Molecular weight ($M_n$) | PDI ($M_w/M_n$) |
| --- | --- | --- | --- |
| 3.5 | 175–225 | 9150 | 1.56 |
| 6.5 | 350–400 | 13450 | 1.37 |
| 14.0 | 550–600 | 26500 | 1.26 |

Conditions: 6–7 mg of CTMS-modified Silica Microparticles (0.88 mmol of initiator); [CuCl]=90.6 mM; [bipy]=280 mM; [benzyl methacrylate]=7.57 M, and p-xylene solvent at 105–110° C.

The molecular weight (Mn) of the grafted polymer, as determined by GPC increased with polymerization time. The molecular weight distribution (Mw/Mn) remained narrow after the initial stage of polymerization. The polydispersity indices are consistent with that expected from living polymerization (PDI<1.5) for the 6.5 h and 14 h cleaved samples, although, the polydispersity of the 3.5 h sample is somewhat higher than 1.5.

Figure 4B:
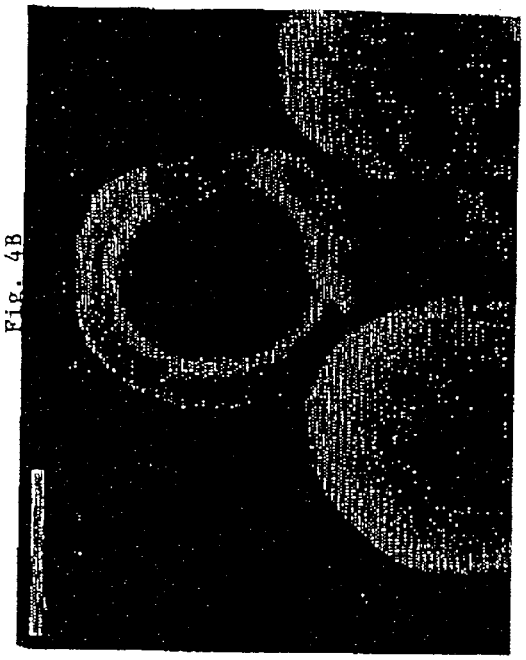
FIGS. 4A–C are scanning electron micrographs of broken microspheres isolated after different polymerization times.
Figure 4C:
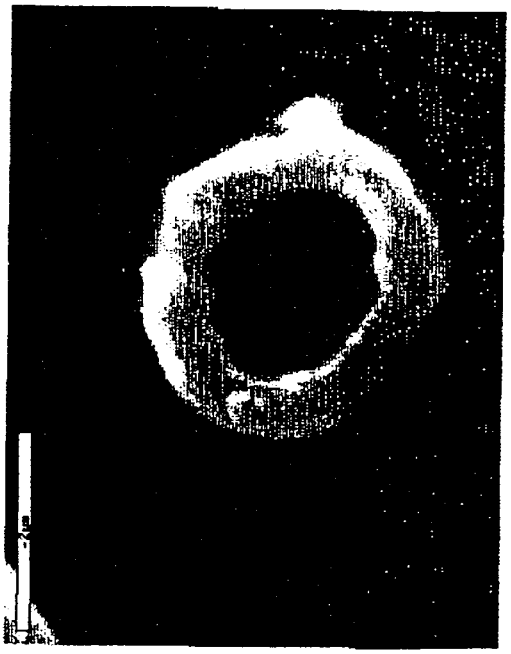
Figure 4A:
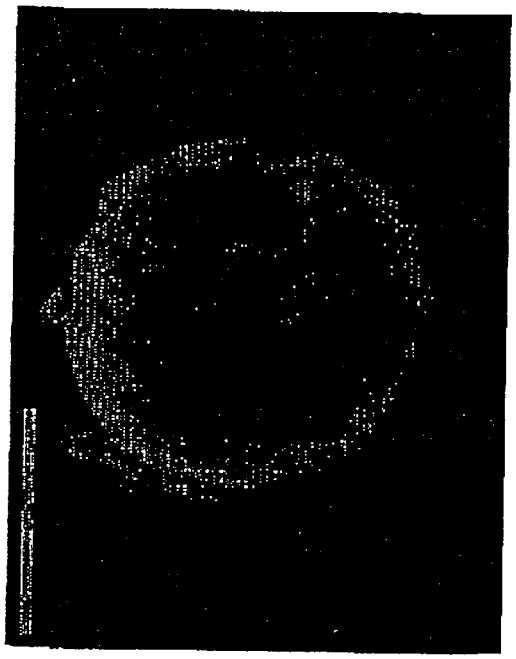

In order to confirm that the microspheres were hollow, they were frozen in liquid nitrogen and then crushed between two glass plates. FIG. 3 shows a SEM image of intact and broken polymer microspheres. Broken hollow PBzMA microspheres produced by varying the polymerization time are shown in FIGS. 4A–C. The shell thicknesses were measured from the SEM micrograph of the broken hollow PBzMA particles, which are given in Table 4. The data reveal that shell thickness increases with increasing polymerization time. Measured shell thicknesses of the samples prepared with different polymerization times were higher than expected based on the calculated values for the fully extended chains from their respective molecular weights. Higher shell thickness values may be due to a number possibilities. First, shell thickness was measured using SEM after the hollow polymer microspheres were freeze-fractured. It is possible that measured shell thickness is artificially high due to distortion of the polymer since the microspheres were frozen and compressed between glass plates prior to fracturing. A second possibility is the formation of polymer inside the pores of the silica templates. Polymer chain attachment and growth at different distances from the template center contributes to the observed shell thickness after etching. The silica core dissolution process may also affect the shell thicknesses. For example, when HF diffuses through the polymer shell and reaches the core, it reacts with silica to form silicon tetrafluoride gas and the polymer chains detach from the surface at their point of attachment. The resulting gas from the interior may produce micro voids inside the polymer shell and result in an increased shell thickness. The detached polymer chains have no solid support, and may also aid in the void generation.

Figure 5:
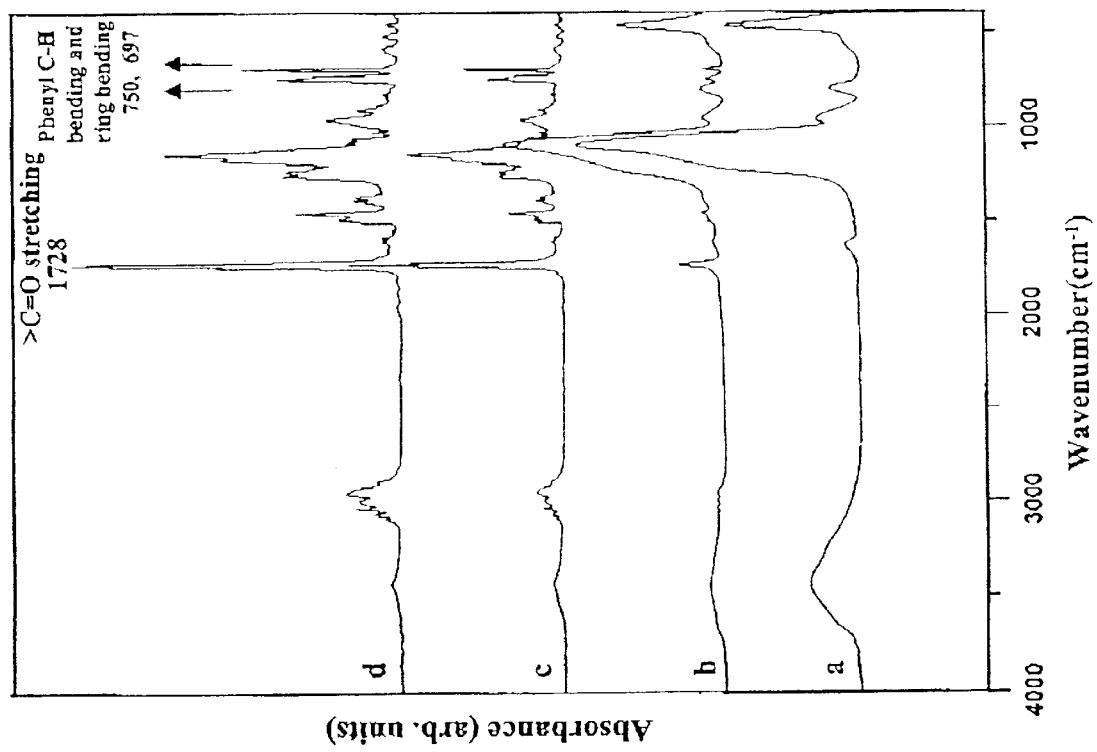
FIG. 5 is a linear plot of a FTIR spectrum. Plot (a) was obtained using pure silica particles; plot (b) was obtained using hybrid poly(benzyl methacrylate)/silica particles; plot (c) was obtained using hollow PBzMA microspheres after silica core etching; and plot (d) was obtained using pure poly(benzyl methacrylate).
Figure 7:
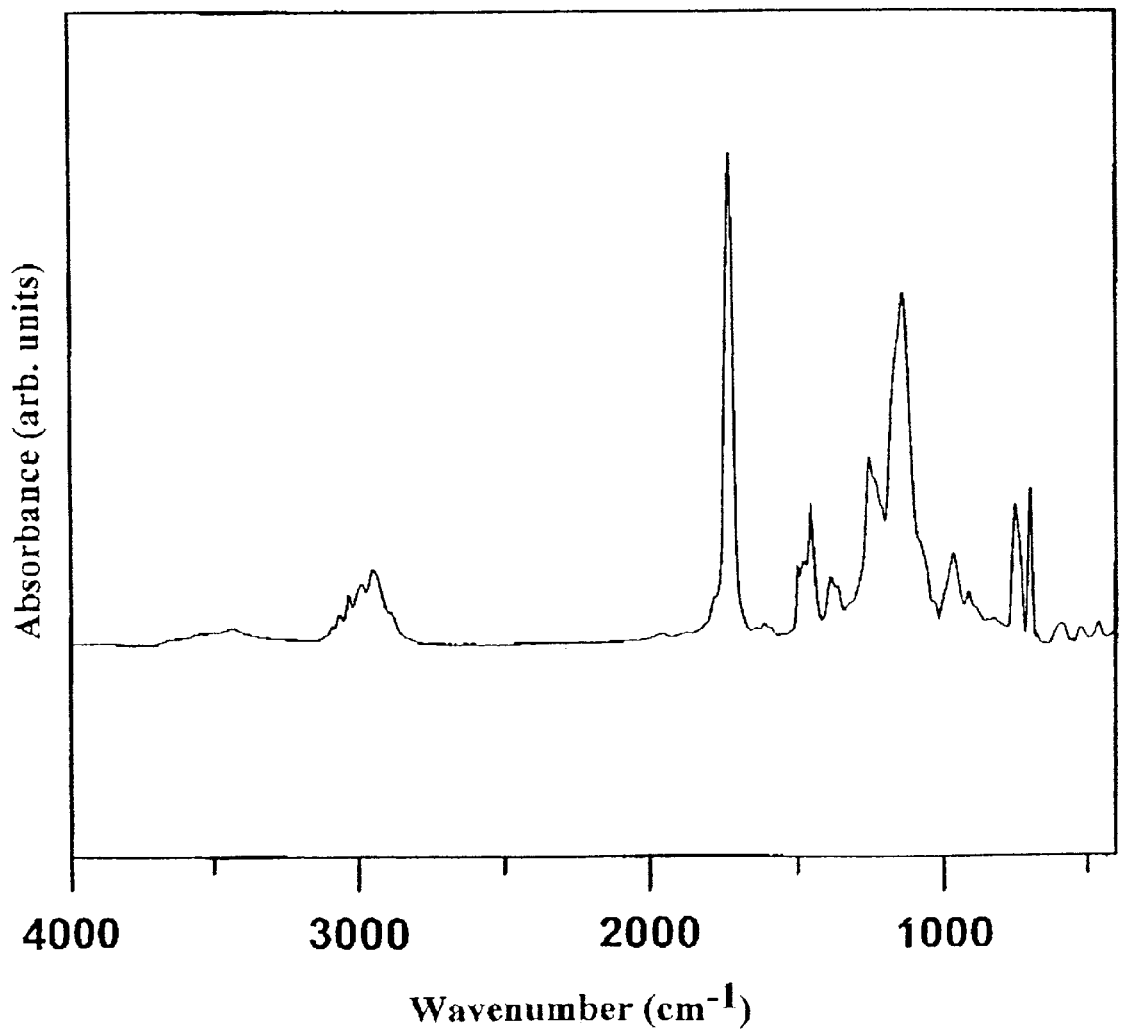
FIG. 7 is a linear graph of a FITR spectrum of the shell cross-linked hollow poly(benzyl methacrylate) microspheres.
Figure 8:
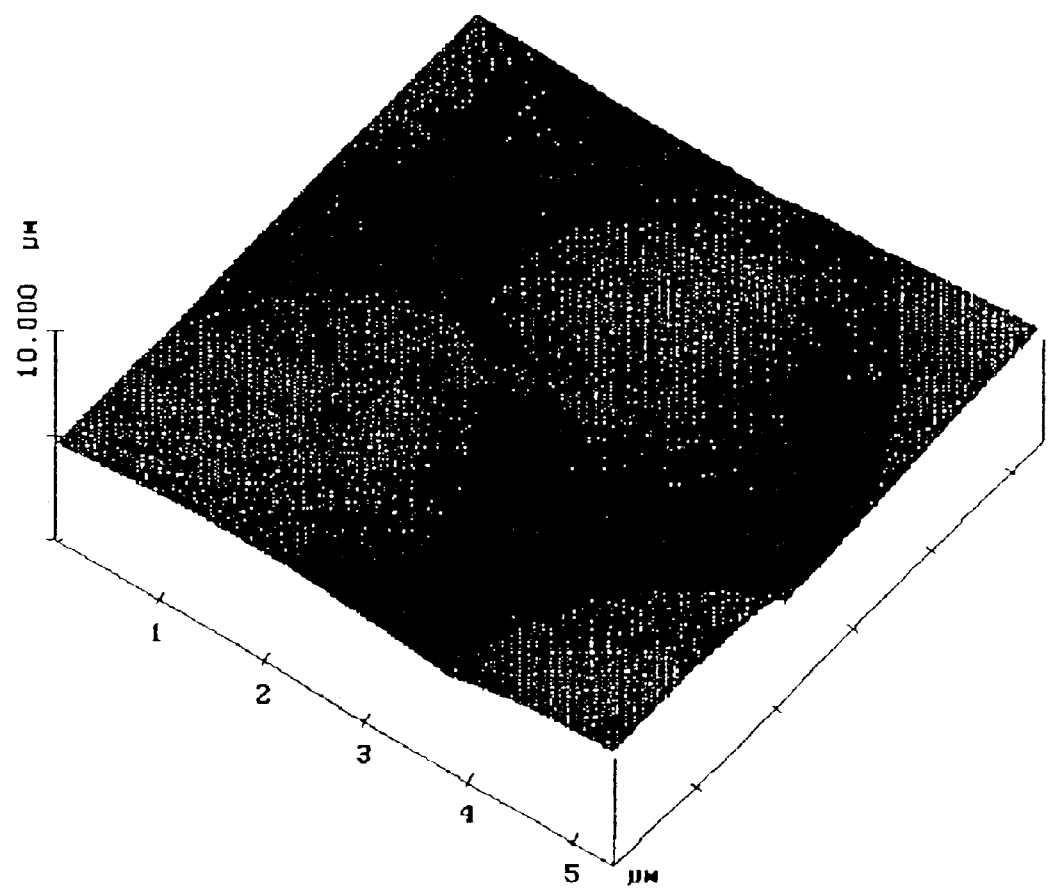
FIG. 8 is a graph of a tapping mode AFM scan of the surface of hollow PBzMA microspheres.

For further confirmation that the polymer microspheres contain little or no silica inside the core, FTIR characterization was performed on etched hollow PBzMA particles and was compared with pure poly(benzyl methacrylate) and neat silica. FIG. 5 shows the FTIR spectra of pure silica, PBzMA coated silica particles and PBzMA particles after etching the silica core. Spectra for polymer-coated silica particles (plot b) reveal bands at 750 and 697 $cm^{-1}$ corresponding to phenyl C—H out-of-plane bending, and benzene out-of-plane ring bending respectively, and the 1728 $cm^{-1}$ carbonyl stretching vibrations characteristic of PBzMA. In addition to the PBzMA signals, a broad intense signal in the 1350–1000 $cm^{-1}$ region corresponds to the solid state vibration of the Si—O—Si bond in silica. The FTIR spectrum of the hollow PBzMA particles (plot c) and cross-linked hollow particles (not shown) is similar to the spectrum of neat PBzMA (plot d) and shows no spectral characteristics of silica, confirming that the silica cores were etched completely.

The data described herein demonstrate that the reliability and predictability of a procedure for making uniform hollow microspheres using surface-initiated controlled/living radical polymerization on silica templates followed by core removal by etching. This method is flexible and enables control over the shell thickness and composition by adjusting polymerization time and monomer concentration. This approach is useful for the fabrication of different shapes of hollow polymeric materials produced from a variety of templates. The method is also useful to produce hollow microspheres containing different polymer layers by the sequential activation of the dormant chain in the presence of different monomers during polymerization.

Nanosphere-Microsphere Assembly Methods for Preparing Core-Shell Composite Microsphere Compositions and Hollow Polymeric Microspheres Colloidal assembly is a process by which particles ranging in size from nanometers to micrometers are organized into structures by mixing two or more particle types. Assembly is controlled by either specific or non-specific interactions between particles. Examples include chemical bonding, biological interactions, electrostatic interactions, capillary action and physical adsorption. The assembly process is performed such that smaller particles assemble around larger ones.

The colloidal assemby method described herein includes specific chemical and biochemical interactions, which are manipulated to control particle assembly. Polymer nanospheres are assembled onto the surface of silica microspheres, and the assembled composite is subsequently heated to a temperature above the Tg of the polymer nanospheres allowing the polymer to flow over the silica microsphere surface, resulting in a uniform core-shell composite. The methods used to assemble 100 and 200 nm diameter amine-modified polystyrene (PS) nanospheres onto 3–10 $\mu$m diameter glutaraldehyde-activated silica microspheres. SFM was used to estimate the packing density of polymer nanospheres on the silica microsphere surfaces. The biospecific interaction between avidin and biotin was also used to control the assembly of PS nanospheres onto silica microspheres. Avidin, a 40 kD glycoprotein, is known to have four high affinity binding sites for the vitamin derivative biotin (MW=244.31). When avidin-labeled PS nanospheres were mixed with biotin-labeled silica in the appropriate number ratio, PS nanospheres assembled onto the microsphere surfaces, covering the microspheres. Thermally annealed composites, produced by heating PS nanospheres-silica microsphere assemblies at temperatures higher than the Tg of PS, were characterized using several analytical techniques. The compositions of the resulting core-shell materials were confirmed by FTIR spectroscopy to be PS-silica composites. The uniformity of the shell material coating was confirmed by scanning electron microscopy (SEM). Core silica particles were etched with hydrofluoric acid to confirm the existence of the shell structure. The resulting hollow polymer microspheres were characterized by transmission electron microscopy (TEM). Composite polymer shell core-shell materials were also produced by mixing PS and poly (methylmethacrylate) nanospheres in varying ratios prior to assembly and annealing.

Uses for Core-shell Composite Compositions

The shell material of a core-shell composite is used to allow dispersal of the core composition in a particular solvent or to protect the core from dissolution in the solvent. For example, core-shell materials are prepared with polymer shells to protect medicines or other materials from dissolution or hydrolysis. Polymer shells are used to stabilize pigments in paints. Core-shell materials are also be useful to strengthen polymeric materials. Other areas of application include the preparation of stationary phases for chromatography or in the preparation of sensing materials. For example, a thin polybutadiene film can be physically adsorbed onto zirconia surfaces and then cross-linked, resulting in a stationary phase for reversed-phase chromatography with exceptional stability at high pH. Core-shell nanoparticles loaded with gadolinium are useful as contrast agents for magnetic resonance imaging.

The following reagents and methods were used to construct microspheres using colloidal assembly.

Reagents

Amine-labeled porous silica microspheres (~3 and ~5 mm diameter) were obtained from Phenomenex Inc. (Torrance, Calif., USA). Amine-modified polystyrene (PS) nanospheres (100 and 200 nm mean diameter) were obtained from Polysciences Inc. (Warrington, Pa., USA). 25% glutaraldehyde solution (aqueous), ethanol and ethylene glycol were obtained from Sigma-Aldrich Chemical Co. (Milwaukee, Wis., USA), Avidin (neutravidin) and biotin were obtained from Molecular Probes Inc. (Eugene, Oreg., USA). N-hydroxysuccinimide (NHS), 1-ethyl-3-(3-dimethylaminopropyl) carbodiimide (EDC) and morpholinoethanesulfonic acid (MES) were obtained from Pierce Chemical Co. (Rockford, Ill., USA). All solutions were prepared using ultra-pure water (Barnstead/Thermolyne, Dubuque, Iowa., USA).

Nanosphere-Microsphere Preparation

Amine-labeled silica microspheres were prepared for assembly by first activating with glutaraldehyde. Prior to activation, approximately 2–6 mg of dry microspheres were placed into an eppendorf tube and washed five times with 1.0 mL of ultra-pure water. Microspheres were cleaned using five cycles of centrifugation, supernatant removal and resuspension in 1.0 mL of ultra-pure water. Microspheres were centrifuged at 5,000×g. The microspheres were then washed two times with 1.0 mL of 50 mM phosphate buffer pH 6.9. The microspheres were then centrifuged again (at 5,000×g), the supernatant removed, and 1.0 mL of a 2.5% glutaraldehyde solution in 50 mM phosphate buffer pH 6.9 was added. The microspheres were suspended, covered with foil and mixed on a vortex shaker for two hours at 4° C. After two hours the microspheres were washed five times with 1.0 mL of ultra-pure water. Microspheres were washed another five times to exchange them into a 50 mM phosphate buffer pH 7.4. The microspheres were stored at 4° C. protected from light until needed for the assembly process. Amine-modified polystyrene nanospheres were similarly prepared for assembly by washing (centrifuging at 18,000×g and resuspending in water) five times with 1.0 mL of ultra-pure water and two times with 1.0 mL of 50 mM phosphate buffer pH 7.4. Nanospheres were stored at 4° C. until they are used in the assembly process. 100 mL of a 2.7% (w/v) suspension of nanospheres are routinely prepared using this procedure.

Biotin-labeled silica microspheres were prepared by treating 2–4 mg of amine-labeled silica microspheres with 1.0 mL of a 5 mM solution of biotin-SE in 0.13 M sodium bicarbonate buffer pH 8.3. The microspheres were suspended and shaken on a vortex shaker for one hour at 4° C. Excess biotin-SE is removed with several cycles of centrifugation (5,000×g), supernatant removal and resuspension with 1.0 mL of 50 mM phosphate buffer pH 7.4. The microspheres were stored at 4° C. until used in the colloidal assembly process. Alternatively, silica microspheres were labeled with avidin by treating 2–4 mg of glutaraldehyde-activated silica microspheres with 1.0 mL of a 2 mg/mL avidin in phosphate buffer pH 6.9 for 2 hours at 4° C. Excess avidin was removed by several cycles of centrifugation and resuspension in 50 mM phosphate buffer pH 7.4.

Biotin labeled nanospheres were prepared as follows: 100 mL of a 2.7% (w/v) suspension of amine-modified polystyrene nanospheres was washed four times with 1.0 mL of ultra-pure water then with 1.0 mL of 0.13 M sodium bicarbonate buffer pH 8.3. Biotin-SE was then added to a final concentration of 5 mM. The nanospheres were shaken on a vortex mixer for one hour at 4° C. Subsequently excess biotin-SE was removed with three cycles of centrifugation/resuspension in 1.0 mL of 50 mM phosphate buffer pH 7.4. When avidin-modified nanospheres were needed for the assembly process, biotin-modified nanospheres (in 50 mM phosphate buffer pH 7.4) were treated with 1.0 mL of a 0.1 mg/mL solution of avidin in 50 mM phosphate buffer pH 7.4. The nanosphere/avidin suspension was gently mixed and then shaken for two hours at 4° C. on a vortex shaker. Subsequently, the nanospheres were washed seven times with 1.0 mL of 50 mM phosphate buffer pH 7.4. Avidin-modified nanospheres were stored at 4° C. until they were used in the assembly process.

Poly(methyl methacrylate)PMMA Nanosphere Preparation

Amine-modified PMMA nanospheres were prepared from carboxyl-modified PMMA nanospheres by conversion of the carboxyl groups to a succinimidyl ester and then treating the nanospheres with ethylenediamine. The procedure was as follows: 100 mL of a 2.7% (w/v) suspension of PMMA nanospheres (80 nm mean diameter) was washed five times with ultra-pure water, then two times with 50 mM MES pH 4.75 containing 0.5% (w/v) NaCl. Next 1.0 mL of a 10 mM NHS/60 mM EDC solution in MES buffer pH 4.75 was added and the nanospheres were suspended and mixed on a vortex mixer on low setting. Mixing continued for one hour at 4° C. in the dark. After one hour, the nanospheres were centrifuged (18,000×g) and the supernatant removed. One mL of fresh NHS/EDC solution was then added and the nanospheres were suspended and mixed. Nanospheres were shaken at 4° C. for another hour. After this time, the nanospheres were immediately centrifuged (18,000×g, 15 minutes), the supernatant was removed and 1.0 mL of a 10 mM ethylenediamine solution in 50 mM phosphate buffer pH 7.4 was added. The nanospheres were suspended and mixed on a vortex shaker. The reaction was allowed to continue at 4° C. for one hour. Following treatment with ethylenediamine, the nanospheres were washed two times with ultra-pure water and then five times with 50 mM phosphate buffer pH 7.4. Amine-modified PMMA nanospheres were stored at 4° C. until used in the assembly process Nanosphere-Microsphere Assembly The colloidal assembly process described herein was controlled by either specific chemical or biochemical interactions. The reactions of amine-modified polystyrene nanospheres with glutaraldehyde-activated silica microspheres and avidin/biotin labeled polystyrene nanospheres with avidin/biotin silica microspheres were used to direct the assembly. Amine-modified PS nanospheres were assembled onto aldehyde-activated silica microspheres as follows: Aldehyde-activated silica microspheres (2–4 mg) were suspended in 50 mM phosphate buffer pH 7.4. Depending on the particle sizes; this suspension contained microsphere concentration of approximately $6.0 \times 10^8$ particles/mL. An appropriate volume of a suspension of amine-modified PS nanospheres in phosphate buffer pH 7.4 was then added so that a 5000:1 number ratio of nanospheres to microspheres was achieved. The suspension was shaken at 4° C. for 12–18 hours on a vortex mixer. Subsequently the product was purified by alternately centrifuging (200×g) and resuspending the assembled product in ultra-pure water. An identical process was followed when assembly was controlled by the biospecific interaction of avidin and biotin labeled nanospheres and microspheres.

Nanosphere-Microsphere Assembly Melting

In order to produce a material with a core-shell morphology the nanosphere-microsphere assemblies were heated at 170–180° C. in ethylene glycol using a temperature-controlled hot plate with a silicone oil bath. As the temperature increased above the glass transition (Tg) of the polymer nanospheres, the polymer melted and then flowed over the surface of the silica microsphere templates. As a result, uniform core-shell materials consisting of a silica core and polymer shell were produced. In order to prepare the nanosphere-microsphere assemblies for melting two milligrams of the assembled product was suspended in 250 mL of ethylene glycol. Ethylene glycol was chosen as the solvent because it has a high boiling point and polystyrene is insoluble in it. This suspension was then added to 750 mL of ethylene glycol in a glass vial maintained at 170–180° C. (silicone oil bath). The mixture was stirred vigorously for 5–10 minutes. The mixture was then removed from the oil bath and sonicated while cooling in room temperature water. The suspension was centrifuged and resuspended in ethanol two times. The suspension was dried on a piece of aluminum and subsequently was brought to a temperature of 170–180° C. The composite was heated at this temperature for 20 minutes. After this time the product was allowed to cool, removed from the metal and resuspended in ultra-pure water. The product was sonicated for two minutes, then centrifuged and resuspended in ultra-pure water an additional two times. To melt the avidin-biotin directed assembly, the composite was first washed with ethanol then applied in a thin layer on an aluminum metal block. The block was then heated at 170–1 80° C. for 20–30 minutes to allow the assembled PS nanoparticles to melt and flow over the silica microsphere surfaces.

Electron Microscopy

SEM and TEM analysis was performed using standard techniques and instrumentation.

Fourier Transform Infra Red (FTIR) Spectroscopy

FTIR (Nicolet Magna-760, Nicolet Instrument Corporation, Madison, Wis.) spectroscopy was used to identify the polymer on the microsphere surfaces. Spectra were obtained at a resolution of 2 cm$^{-1}$ and averages of 64–100 spectral/scans (for enhanced signal) were obtained in the wavenumber range 400–4000 cm$^{-1}$. All samples were prepared for analysis using a KBr pellet. Pellets were prepared using a 50:1 weight ratio of KBr to sample. All spectra were acquired at room temperature.

Scanning Force Microscopy

Surfaces of composite microspheres were imaged using a Digital Instruments Nanoscope IIIa scanning probe microscope. (Digital Instruments Inc., Santa Barbara, Calif., USA). Images were acquired in Tapping mode under standard conditions.

Nitrogen analysis

Weight percent nitrogen was determined by Galbraith Laboratories Inc. (Knoxville, Tenn., USA) Oven-dried samples of amine-labeled silica microspheres and amine-modified polymer nanospheres were submitted for analysis.

Chemical Etching of Core-shell Composites

The silica cores were etched using an 8% aqueous solution of hydrofluoric acid. Approximately 1 mg of polystrene-silica composite was suspended in 1.0 mL of ultra-pure water. Concentrated hydrofluoric acid (50%w/v) was then added to bring the total HF concentration to 8%. The suspension was allowed to stand for 20 minutes to assure complete removal of the silica cores. The composite was then washed five times with 1.0 mL of ultra-pure water. The resulting hollow polymer microspheres were then air dried on glass slides prior to SEM or TEM analysis.

Characterization of Microspheres after Colloidal Assembly

Figure 12:
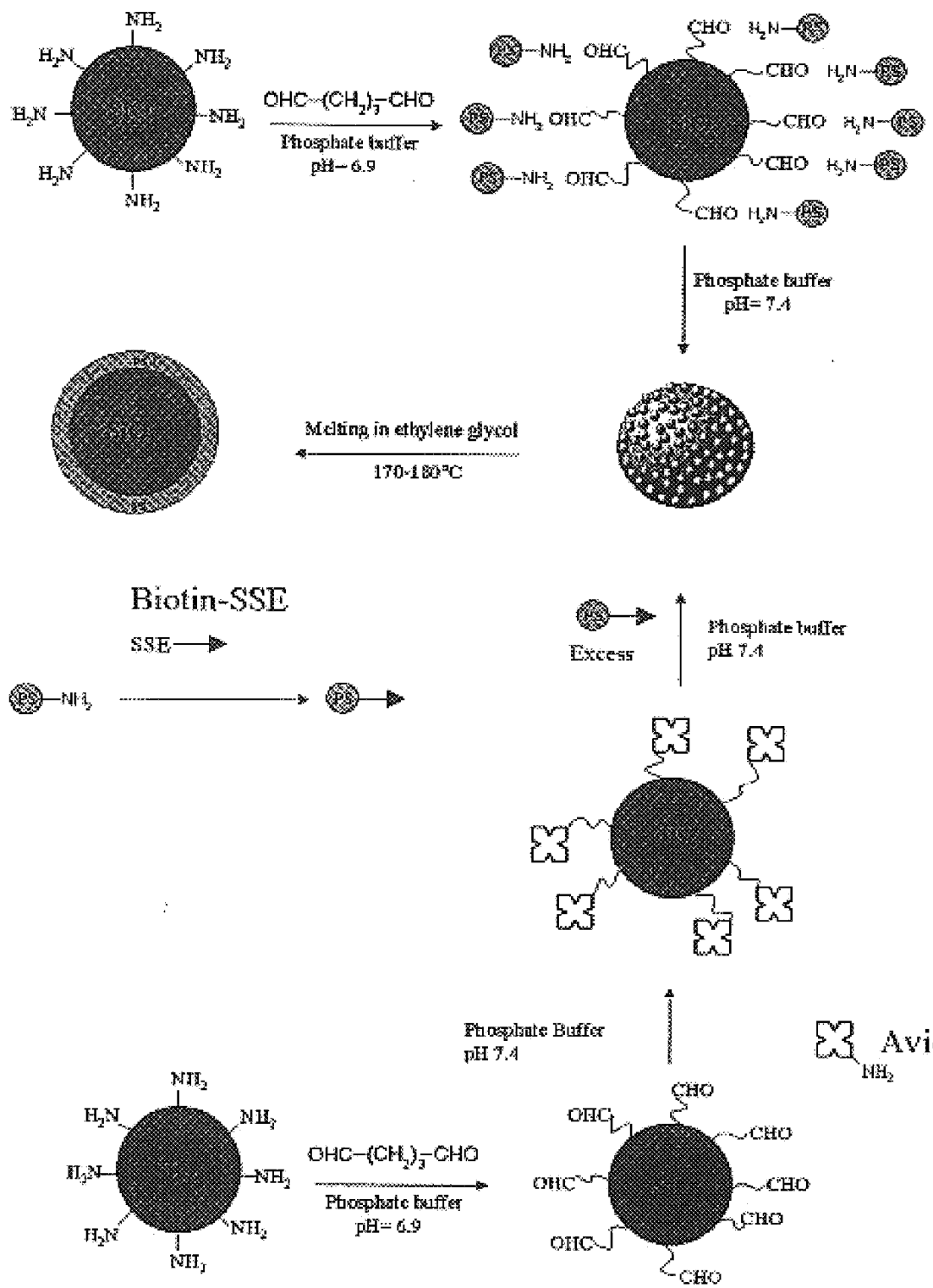
FIG. 12 is a diagram showing a scheme for assembling composite materials via both glutaraldehyde chemistry and biospecific interactions. The top section illustrates assembly starting with amine-labeled silica. Glutaraldehyde treatment followed by reaction with amine-modified polystyrene nanospheres results in a silica-polymer composite that can be heated at 170–180° C. to melt the polystyrene. A core-shell material composed of a silica core and polystyrene shell is produced. The bottom section illustrates assembly of biotin-labeled polystyrene nanoparticles onto avidin-coated silica microspheres.

The general procedure for the colloidal assembly of polymer nanospheres with silica microspheres is shown in FIG. 12.

The assembly process was performed by mixing a suspension of complementary types of nanospheres and microspheres at 4° C. for 12–18 hours. The assembly process was designed to pack as many nanospheres onto the microsphere surface as possible. The numbers of nanospheres to be packed on the microsphere surfaces was calculated by dividing the theoretical microsphere surface area by the cross-sectional area of a plane bisecting a nanosphere. The resulting value was used to determine the minimum number of nanospheres needed in suspension for each microsphere present. The number of nanospheres required to completely cover a microsphere can be calculated using known methods, e.g., Ottewill et al.,1997, Colloid Polym. Sci. 275:274–283. The calculation is based on hexagonal close packing of the nanospheres onto a planar surface. Following assembly, the composites were heated at 170–180° C. to melt the polymer nanospheres (FIG. 12).

Figure 1A:
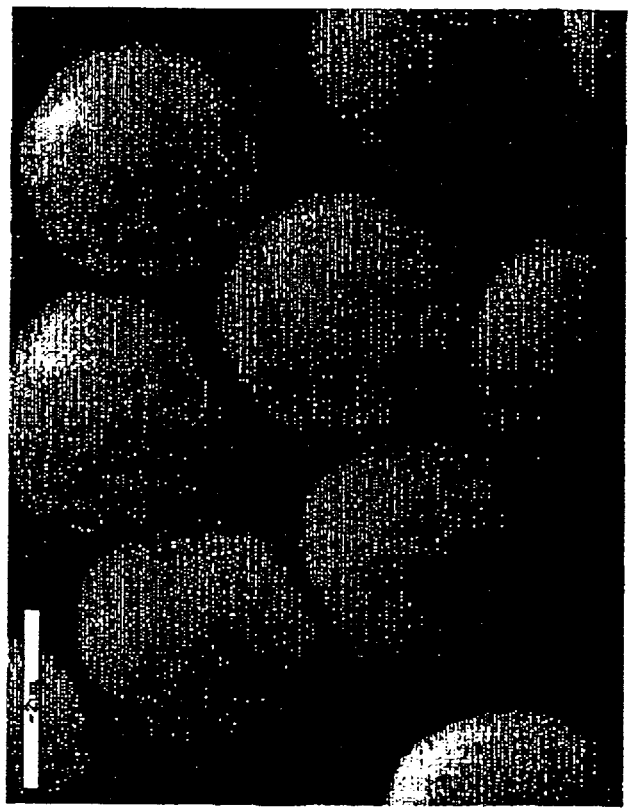
Figure 13:
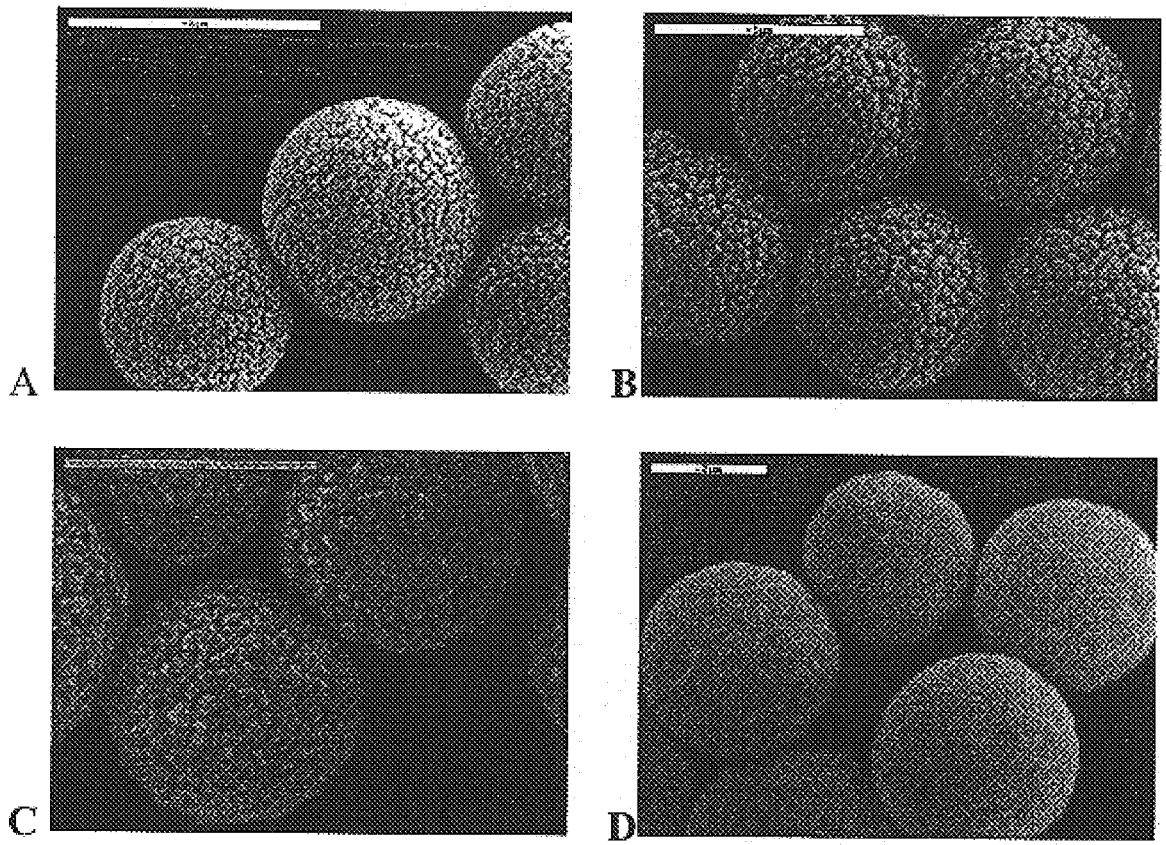
FIGS. 13A–D are scanning electron micrographs of particle assemblies.
Figure 14:
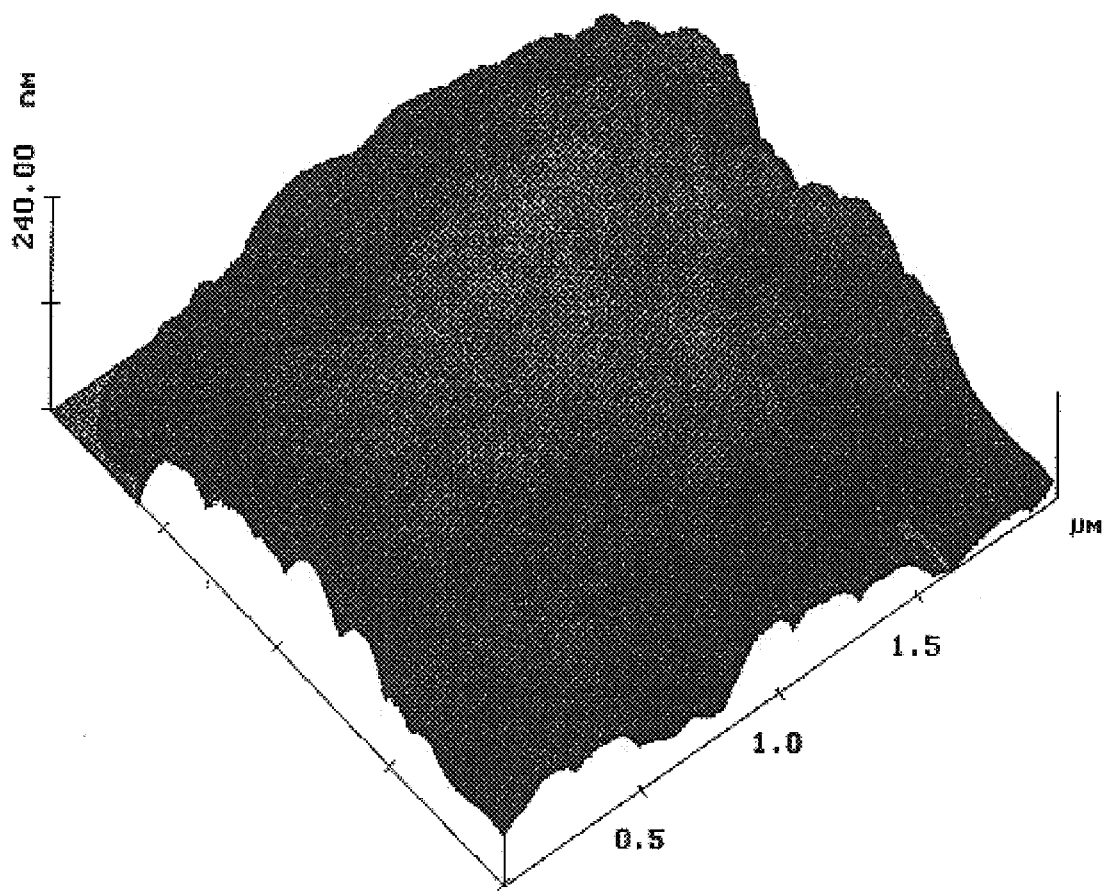

After heating, the polymer melts and flows over the microsphere surfaces to yield uniform core-shell materials consisting of a silica core and a polymer shell. Representative SEM images of these materials are shown in FIGS. 13A–D. An SEM image of 100 nm amine-modified PS particles assembled onto 3 μm diameter glutaraldehyde-activated silica microspheres is shown in FIG. 1A. FIG. 13B is an SEM of 200 nm diameter amine-modified PS particles assembled onto 5 μm diameter silica microspheres. An SEM of 100 nm avidin-labeled nanospheres assembled onto 3 μm diameter biotin-labeled silica microspheres is shown in FIG. 13C. Tapping mode SFM was used to image the surfaces of composite microspheres (5 μm diameter) that were assembled with 200 nm PS nanospheres. The SFM scan shows that the 200 nm PS particles are assembled in a dense array on the surface of the microspheres (FIG. 14).

The packing density of the polymer nanospheres on the surface of the silica microspheres is an important variable in the formation of a uniform polymer shell around the silica microspheres. Packing density was easily and reliably controlled when the assembly process was controlled by amine-aldehyde chemistry. The packing density was slightly more variable when assembly was controlled by the interactions of avidin and biotin-labeled colloidal particles. In some cases, aggregation may arise during the synthesis of the avidin-labeled nanospheres, because the nanospheres are first labeled with biotin and then subsequently treated with an excess of avidin. Cross-linking of nanospheres may occur if the concentration of nanospheres in the suspension is too high relative to the amount of avidin used. Aggregation may also occur when insufficient numbers of biotin-labeled nanospheres are mixed with avidin-labeled silica microspheres. Despite these factors associated with the use of avidin-biotin, the assembled composites are comparable in uniformity of thickness to those formed when amine-glutaraldehyde is used to control the assembly process.

Figure 15:
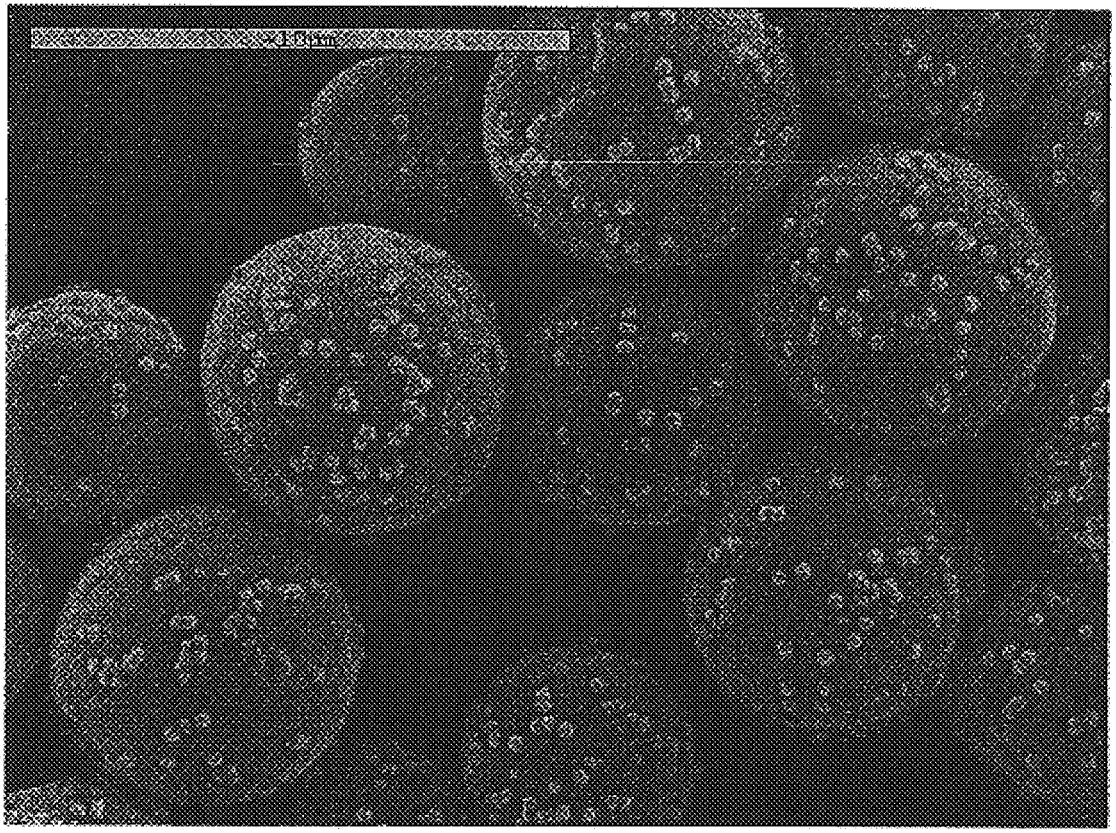
FIG. 15 is a scanning electron micrograph of a nonspecific binding control. 100 nm amine-modified nanospheres were mixed with amine-labeled silica microspheres under conditions identical to those in the assembly process.

Since the methods used to control the assembly process involve specific chemical and biochemical interactions, it was necessary to verify that the assembled composites were the result of these specific interactions between the particles and not to non-specific interactions. Non-specific binding during the assembly process was minimal for both the amine-glutaraldehyde and avidin-biotin methods. Percentages of non-specific binding were estimated based on the theoretical maximum number of nanospheres that could cover one-half of a microsphere surface. The number of nanospheres visible in SEM images of controls assembled with non-specific binding were counted and taken as the percentage of the theoretical maximum. Approximately 10–12% non-specific binding was observed when amine-modified nanospheres were mixed with amine-coated silica microspheres. The weight % nitrogen was 0.73% and <0.5% for the amine-labeled silica microspheres and amine-modified polystyrene nanospheres respectively. An SEM image of microspheres prepared using non-specific binding (control) is shown in FIG. 15.

Other non-specific binding controls included mixing unmodified polystyrene nanospheres with aldehyde-activated silica microspheres, amine-modified polystyrene nanospheres with unmodified silica microspheres and unmodified polystyrene nanospheres with unmodified silica microspheres. In each of these cases, non-specific binding was <1%. A non-specific binding control for avidin-biotin directed assembly was performed by mixing avidin-labeled nanospheres with avidin-labeled silica microspheres. Approximately 1% non-specific binding was observed.

The assembled composites prepared by either the amine-glutaraldehyde or avidin-biotin methods were very stable (as observed by SEM). No noticeable changes in the surfaces of the materials were observed upon several weeks storage in solution at room temperature or at 4–8° C. Suspension in ethanol or ethylene glycol had no effect unless the temperature was increased above the glass transition (Tg) of PS. Stability of the assembled composites in ethylene glycol was important since the melting procedure was performed at elevated temperature in this solvent.

The polystyrene nanosphere/silica microsphere assemblies were heated in ethylene glycol under the premise that the polymer nanospheres would melt and the polymer would flow over the silica microsphere surfaces, producing a core-shell composite with a uniform polymer coating. Ethylene glycol was chosen as the solvent for heating the materials because it has a high boiling point and because polystyrene and many other polymers are insoluble in it. Microsphere aggregation during the heat treatment was minimized by controlling the concentrations of microspheres in solution. Annealing the composites on an aluminum metal block after the initial heating in ethylene glycol helped to improve the uniformity of the polymer coating. Melting of the 100 nm PS/3 µm silica microsphere assembly (Figure 3.3a) at high temperature in ethylene glycol, followed by heating on an aluminum block results in the uniform PS-silica core-shell composite shown in FIG. 13D.

Avidin-biotin assembled composites could only be melted on an aluminum metal surface because melting in an ethylene glycol solution did not result in uniformly coated core-shell composites. This result may be due to the instability of the avidin-biotin linkage in solution at the high temperatures used to melt the nanospheres, which causes them to dissociate.

Figure 16:
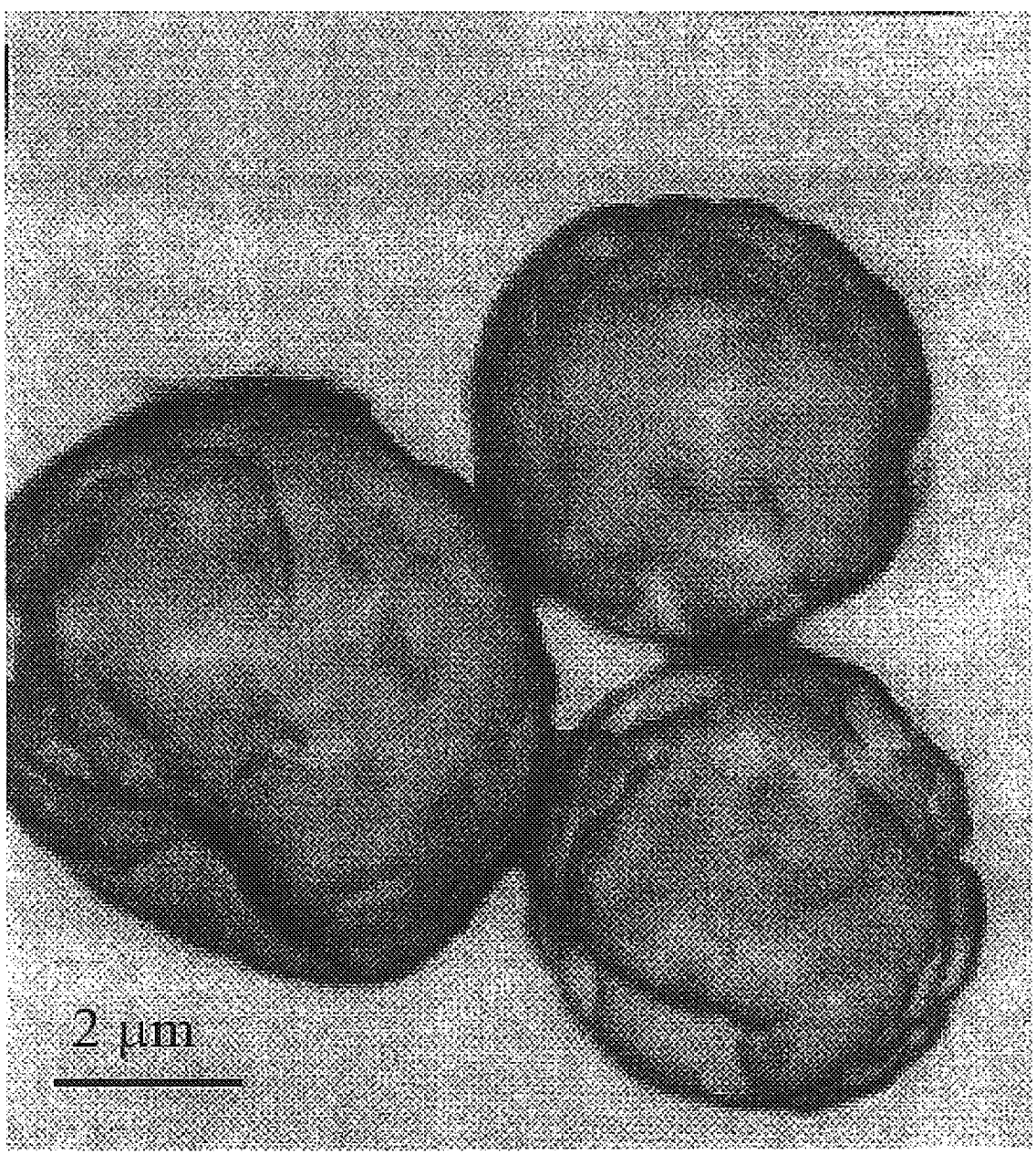
FIG. 16 is a transmission electron micrograph (TEM) of hollow microspheres after chemical etching of core-shell materials produced by assembly/melting of 200 nm PS nanospheres with 5 µm diameter silica microspheres.

To verify that polystyrene was coating the silica microspheres, two independent evaluations were performed. A time study was conducted by heating the polystyrene nanoparticle-coated silica microspheres in ethylene glycol and then removing aliquots of assembled microspheres at various times during the course of the 30-minute heating. SEM images showed that nanoparticles remained attached to the silica microsphere surface after five minutes. As the heating time increased, the spherical nanoparticles melted and gradually filled in the spaces between nanoparticles until the surface was uniformly coated. The integrity of the polymer shells was determined by removing the silica cores by chemical etching with hydrofluoric acid. After chemical etching, hollow polymer shells were all that remained of the composite. The hollow polymer microspheres produced remained intact after sonication in ultra-pure water and centrifugation at 2,000×g. This result provides additional evidence of polymer coating, since the silica microspheres do not survive such treatment. A TEM of hollow polymer shells produced by assembling 200 nm PS nanospheres onto 3 µm silica microspheres, followed by annealing and chemical etching is shown in FIG. 16.

Figure 17:
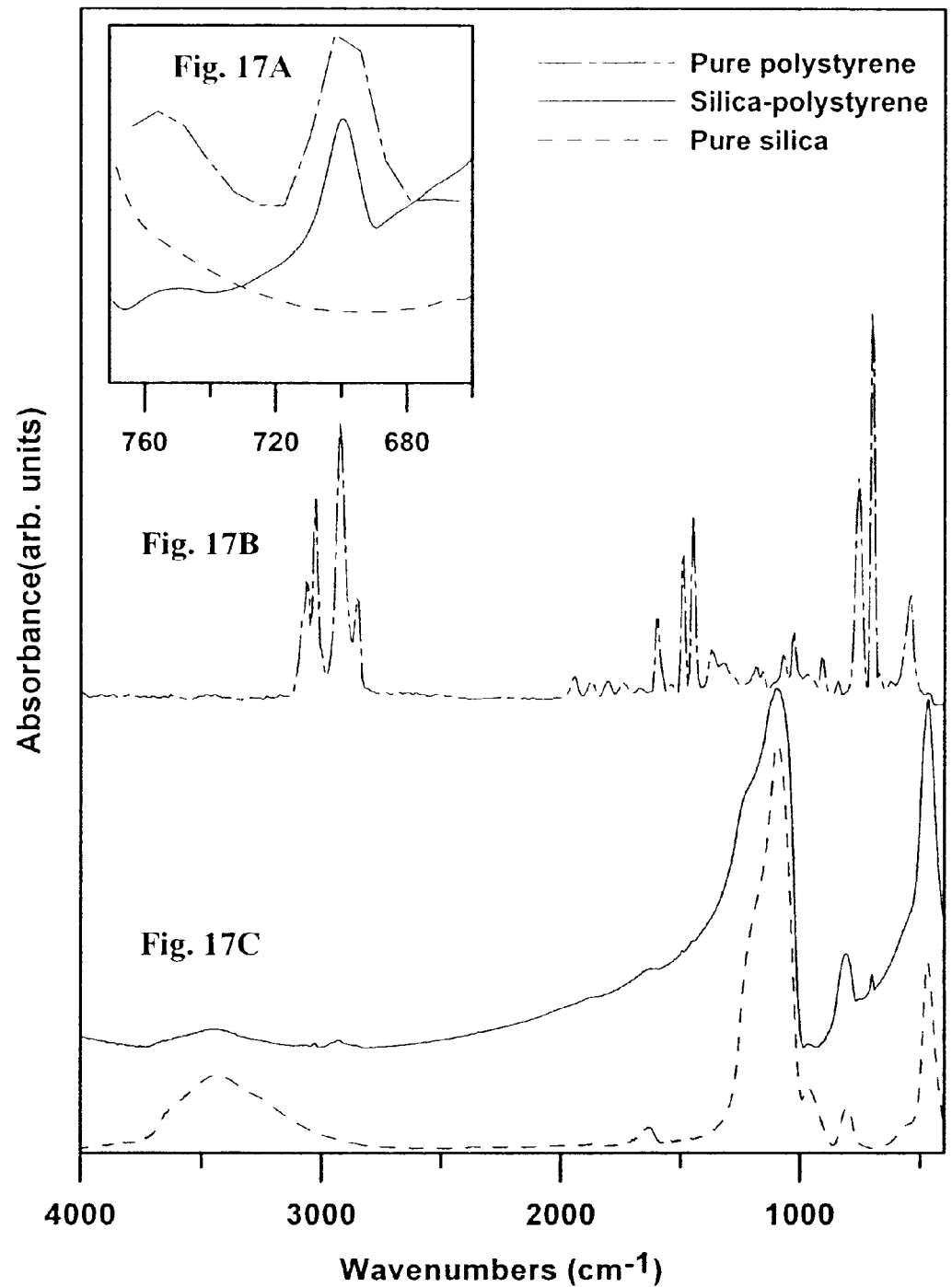
FIGS. 17A–C are line graphs showing data from FTIR spectroscopy of pure polystyrene (FIG. 17A), melted PS-silica composite (FIG. 17B) and aldehyde-activated silica (FIG. 17C).

FTIR spectra (FIG. 17) of the PS-silica core-shell composites provide additional evidence that the melting procedure results in polymer coated microspheres. The methods described herein provide considerable control in the assembly process to consistently yield core-shell compositions and hollow microspheres in which the thickness of the shell is essentially uniform, i.e., the thickness varies less than 10%.

Figure 18:
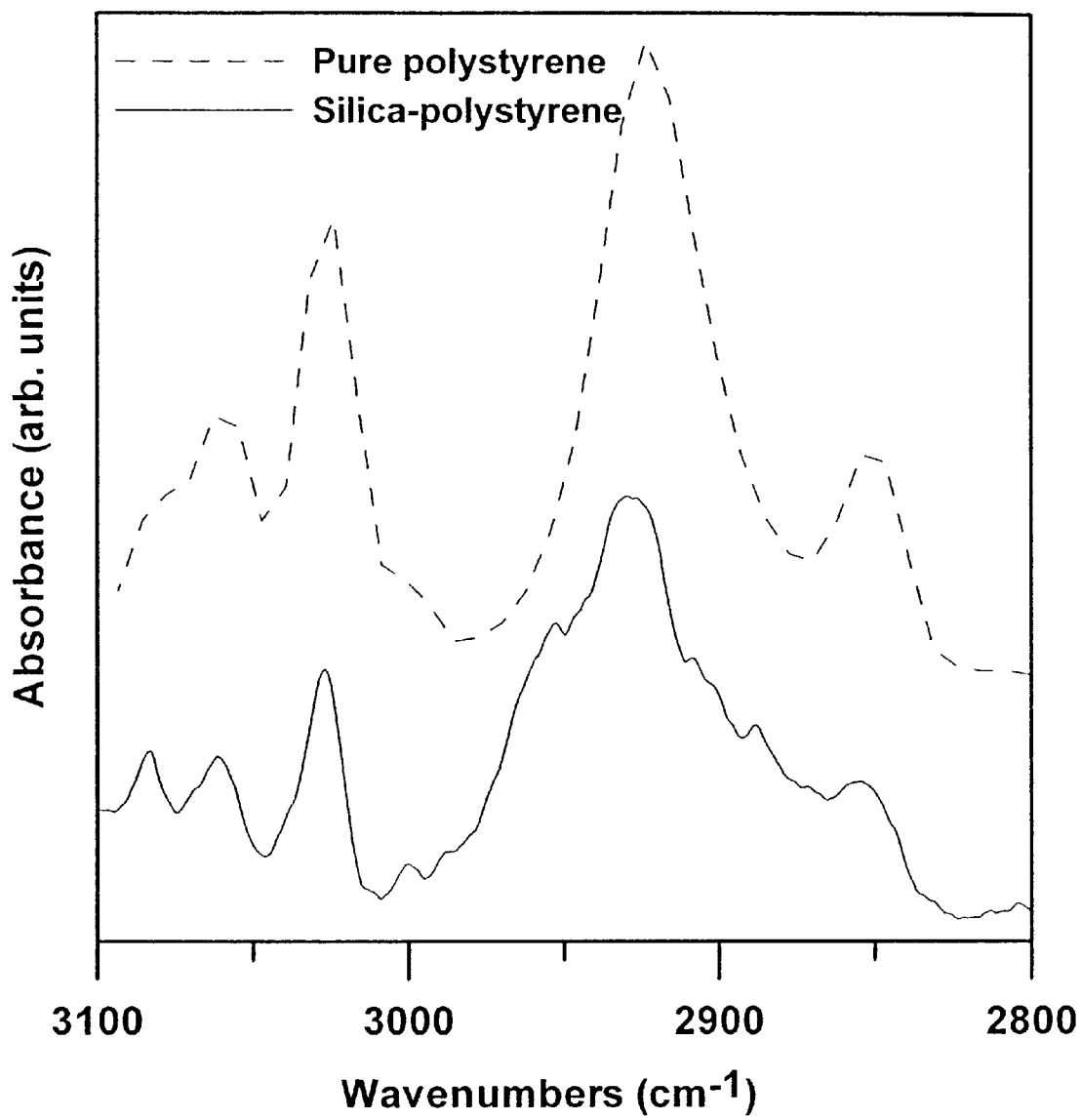
FIG. 18 is a line graph showing a comparison of FTIR spectra of pure polystyrene and PS-silica composite. The spectra shown are in the range of 2850 $cm^{-1}$ to 2950 $cm^{-1}$. Peaks in this wavenumber range correspond to the aliphatic C-H stretching of polystyrene.

The spectra reveal bands at 750 cm$^{-1}$ and 697 cm$^{-1}$, which correspond to the phenyl C—H out-of-plane bending and benzene out-of-plane ring bending respectively. Both of these resonances are characteristic of polystyrene and are absent from the starting silica microspheres. Aliphatic C—H stretching resonances of polystyrene (2900 cm$^{-1}$) can be seen in the FTIR spectra shown in FIG. 18.

Figure 19:
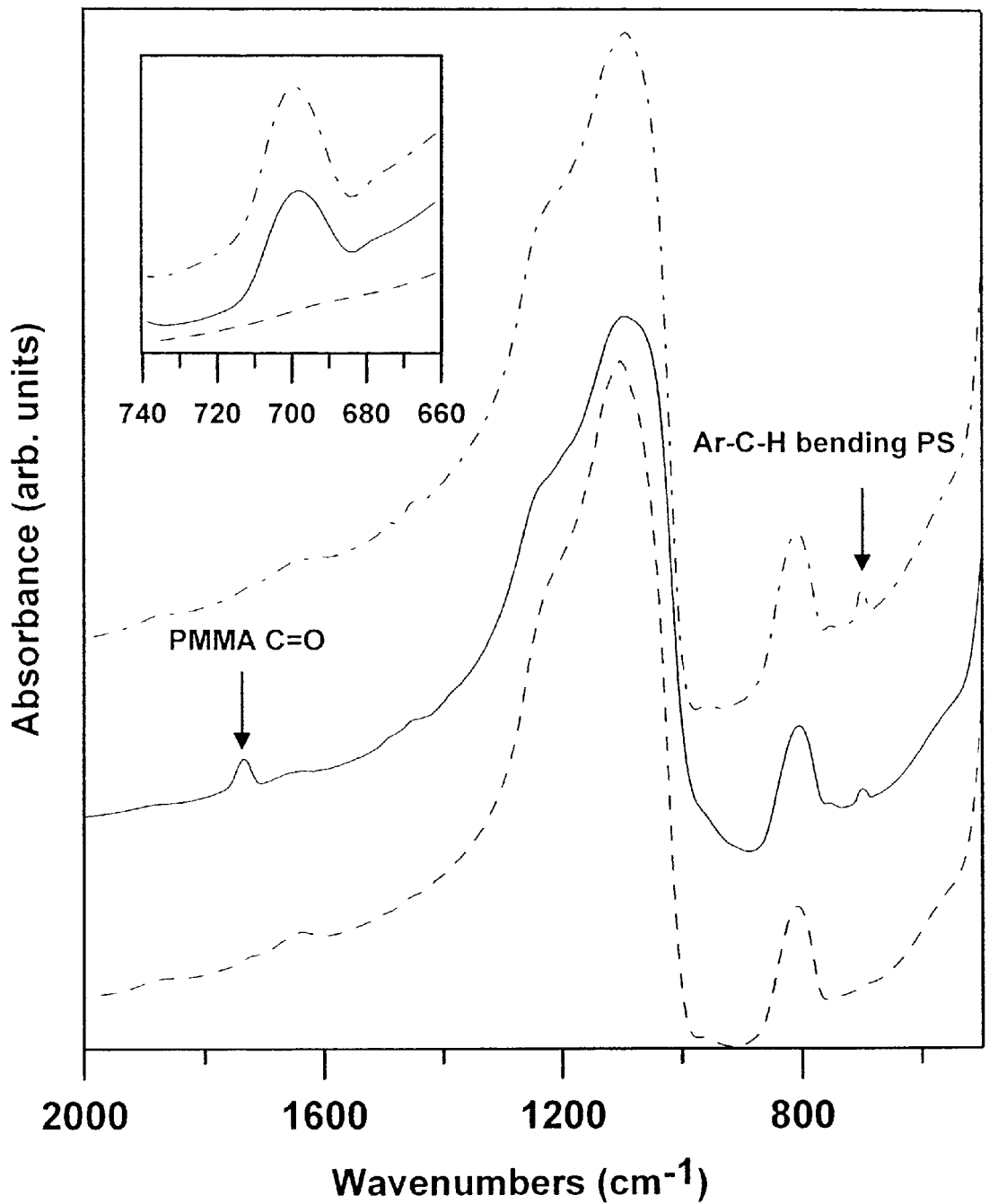
FIG. 19 is a line graph showing FTIR spectra of different core-shell composites. The top spectrum (PS/silica composite) has peaks corresponding to both silica and PS, while the middle spectrum (PS/PMMA/silica composite) has an additional peak corresponding to the carbonyl of the PMMA polymer. The bottom spectrum is from plain silica microspheres.

A 50:50 mix of PS and poly (methylmethacrylate) nanospheres resulted in an assembled composite with a polymer nanosphere composition corresponding to this ratio. This assembly was heated at 170–180° C. in ethylene glycol to melt both nanosphere types assembled on the silica microspheres. The resulting core-shell composite was confirmed by FTIR spectroscopy to be a PS-PMMA composite (FIG. 19).

The data described herein indicate that assembled materials predictably produce core-shell composites, e.g., those containing a silica core and a polystyrene shell of essentially uniform thickness. The methods can be used to create a shell that is a composite of multiple polymer types by mixing polymer nanospheres in the ratio desired prior to assembly. Such materials have applications in both analytical and materials chemistry development. Core-shell composite materials are useful in the design of layered sensing materials, the production of stationary phases for chromatographic separations or the development of drug delivery systems.

Nanosphere/microsphere assembly accesses novel materials a reliable and flexible procedure. By selecting the compositions of the particles used in the assembly procedure, considerable control is gained over the physical and chemical properties of the resulting composites. Additional control over physical/chemical properties is achieved by the ability to melt assembled polymer particles yielding uniform silica core/polymer shell composite materials. The use of specific chemical/biochemical interactions to control the assembly process of colloidal particles has several advantages over the use of electrostatic interactions or heterocoagulation to prepare core-shell composites. One advantage is that a wider range of materials may be assembled when specific interactions are used. For example, particles that are not charged or have the same charge are assembled using this technique. Amine-modified PS nanospheres are assembled onto amine-labeled silica by activating the silica surface with a cross-linking dialdehyde. Another advantage is the improved stability of the assembled products when covalent or strong biospecific interactions are employed. The stability of the bonds between the particles allows the use of a wider range of pH's, ionic strengths and solvents in the assembly process.

Other embodiments are within the following claims.

What is claimed is:

1. A method for preparing a hollow microsphere, comprising:

providing a substrate comprising a plurality of hydroxyl groups;

attaching an initiator agent to said hydroxyl groups to form attached initiator agents;

reacting the attached initiator agents with a polymerizable unit under living polymerization conditions to form a polymer shell over said substrate, said polymerization being confined to a surface of said substrate; and exposing said substrate to an etching agent for a time sufficient to allow for removal of said substrate from said polymeric shell to form a hollow microsphere.

2. The method of claim 1, wherein said substrate is silica.

3. The method of claim 1, wherein said substrate is selected from the group consisting of silica, alumina, mica, and clay.

4. The method of claim 1, further comprising exposing said polymer shell to a crosslinking agent.

5. The method of claim 1, wherein said polymerizable unit is selected from the group consisting of acrylonitrile, styrene, benzyl methacrylate, phenyl methacrylate, ethyl methacrylate, divinyl benzene, 2-hydroxyethyl methacrylate, cyclohexyl methacrylate, p-methyl styrene, acrylamide, methacrylamide, methacrylonitrile, hydroxypropyl methacrylate, methoy styrene, N-acrylylglycinamide, and N-methacrylylglycinamide.

6. The method of claim 1, wherein said polymerizable unit is selected from the group consisting of styrene-PMMA, benzyl methacrylate-PMMA, styrene-PHEMA, styrene-PEMA, styrene-methacrylate, and styrene-butylacrylate.

7. The method of claim) wherein said initiator agent is selected from the group consisting of phenyl ethyl chloride, phenyl ethyl bromide, phenyl sulfonyl chloride, and 2-bromoethylisobutyrate.

* * * * *